(12) United States Patent
Stupp et al.

(10) Patent No.: US 7,683,025 B2
(45) Date of Patent: Mar. 23, 2010

(54) SYNTHESIS AND SELF-ASSEMBLY OF ABC TRIBLOCK BOLA PEPTIDE AMPHIPHILES

(75) Inventors: Samuel I Stupp, Chicago, IL (US); Randal C. Claussen, Wilmette, IL (US); Bryan M. Rabatic, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/534,266

(22) PCT Filed: Nov. 14, 2003

(86) PCT No.: PCT/US03/36397

§ 371 (c)(1),
(2), (4) Date: Oct. 13, 2005

(87) PCT Pub. No.: WO2004/046167

PCT Pub. Date: Jun. 3, 2004

(65) Prior Publication Data

US 2006/0110437 A1    May 25, 2006

Related U.S. Application Data

(60) Provisional application No. 60/426,189, filed on Nov. 14, 2002.

(51) Int. Cl.
*A61K 38/06*    (2006.01)
(52) U.S. Cl. .................. 514/2; 514/17; 514/18; 514/19; 530/345; 424/450
(58) Field of Classification Search .............. 514/2, 514/17–19; 530/345; 424/450
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,130,123 A | 7/1992 | Reynolds et al. | |
| 5,208,111 A | 5/1993 | Decher et al. | |
| 5,670,483 A | 9/1997 | Zhang et al. | |
| 5,733,868 A | 3/1998 | Peterson et al. | |
| 5,843,780 A | 12/1998 | Thomson | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A * | 8/2000 | Fields et al. | 530/326 |
| 6,156,321 A | 12/2000 | Thorpe et al. | |
| 6,181,909 B1 | 1/2001 | Burstein et al. | |
| 6,201,065 B1 | 3/2001 | Pathak et al. | |
| 6,265,539 B1 * | 7/2001 | Arlinghaus | 530/326 |
| 6,269,368 B1 | 7/2001 | Diamond | |
| 6,270,765 B1 | 8/2001 | Deo et al. | |
| 6,309,862 B1 | 10/2001 | Jarekrans et al. | |
| 6,391,297 B1 | 5/2002 | Halvorsen | |
| 6,444,723 B1 | 9/2002 | Kline | |
| 6,458,924 B2 * | 10/2002 | Knudsen et al. | 530/324 |
| 6,473,730 B1 | 10/2002 | McKeown et al. | |
| 6,548,048 B1 | 4/2003 | Cuthbertson et al. | |
| 6,548,630 B1 | 4/2003 | Zhang et al. | |
| 6,562,619 B1 | 5/2003 | Gearhart et al. | |
| 6,800,481 B1 | 10/2004 | Holmes et al. | |
| 6,855,329 B1 | 2/2005 | Shakesheff et al. | |
| 6,890,654 B2 | 5/2005 | Stupp et al. | |
| 7,371,719 B2 | 5/2008 | Stupp et al. | |
| 7,390,526 B2 | 6/2008 | Stupp et al. | |
| 7,534,761 B1 | 5/2009 | Stupp et al. | |
| 7,544,661 B2 | 6/2009 | Stupp et al. | |
| 7,554,021 B2 | 6/2009 | Stupp et al. | |
| 2002/0007217 A1 | 1/2002 | Jacob et al. | |
| 2002/0046018 A1 | 4/2002 | Marcu et al. | |
| 2002/0142277 A1 | 10/2002 | Burstein et al. | |
| 2002/0160471 A1 | 10/2002 | Kisiday et al. | |
| 2003/0059906 A1 | 3/2003 | Hubbell et al. | |
| 2003/0092672 A1 * | 5/2003 | Darcy et al. | 514/54 |
| 2003/0176335 A1 | 9/2003 | Zhang et al. | |
| 2004/0001893 A1 | 1/2004 | Stupp et al. | |
| 2004/0018961 A1 | 1/2004 | Stupp et al. | |
| 2004/0022718 A1 | 2/2004 | Stupp et al. | |
| 2004/0258726 A1 | 12/2004 | Stupp et al. | |
| 2005/0208589 A1 | 9/2005 | Stupp et al. | |
| 2005/0209145 A1 | 9/2005 | Stupp et al. | |
| 2005/0214257 A1 | 9/2005 | Zhao et al. | |
| 2005/0272662 A1 | 12/2005 | Stupp et al. | |
| 2006/0149036 A1 | 7/2006 | Stupp et al. | |
| 2006/0247165 A1 | 11/2006 | Stupp et al. | |

FOREIGN PATENT DOCUMENTS

| | | |
|---|---|---|
| WO | 93/22343 A1 | 11/1993 |
| WO | 94/02506 A1 | 2/1994 |
| WO | 97/14713 A1 | 4/1997 |
| WO | 97/20639 A1 | 6/1997 |
| WO | 98/07752 A1 | 2/1998 |
| WO | 99/36107 | 7/1999 |
| WO | 99/36107 A1 | 7/1999 |
| WO | 99/55383 A2 | 11/1999 |
| WO | 00/13710 A2 | 3/2000 |
| WO | 00/44808 A1 | 8/2000 |
| WO | 00/45831 A1 | 8/2000 |
| WO | 00/52145 A2 | 9/2000 |
| WO | 00/64481 A1 | 11/2000 |
| WO | 02/062969 A2 | 8/2002 |
| WO | 03/040336 A2 | 5/2003 |
| WO | 03/054146 A2 | 7/2003 |
| WO | 03/070749 A2 | 8/2003 |
| WO | 03/084980 A2 | 10/2003 |
| WO | 03/090255 A2 | 10/2003 |
| WO | 01/00650 A1 | 1/2004 |
| WO | 2004/003561 A1 | 1/2004 |
| WO | 2004/018628 A2 | 3/2004 |
| WO | 2004/024778 A2 | 3/2004 |
| WO | 2004/046167 A2 | 6/2004 |
| WO | 2004/072104 A2 | 8/2004 |
| WO | 2004/091370 A2 | 10/2004 |
| WO | 2004/106359 A2 | 12/2004 |
| WO | 2005/003292 A2 | 1/2005 |
| WO | WO 2005/014619 A2 | 2/2005 |
| WO | 2005/056039 A1 | 6/2005 |
| WO | 2005/056576 A2 | 6/2005 |
| WO | 2006/096614 A2 | 9/2006 |

OTHER PUBLICATIONS

Kogiso, M. (Biochimica et Biophysica Acta, General Subjects 1475(3), 346-352, 2000).*

Brown, Walter E. Dec. 15, 1962. "Octacalcium Phosphate and Hydroxyapatite." *Nature.* vol. 196, pp. 1048-1050.

Liang, W. Y. and A. D. Yoffe. Jan. 8, 1968. "Transmission Spectra of ZnO Single Crystals." *Physical Review Letters.* vol. 20, No. 2, pp. 59-62.

Greenfield, Norma and Gerald D. Fasman. Oct. 1969. "Computed Circular Dichroism Spectra for the Evaluation of Protein Conformation." *Biochemistry.* vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem.* vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." *Journal of the American Chemical Society.* vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science.* vol. 195, No. 4275, pp. 302-304.

Biesecker, G., J. Ieuan Harris, J. C. Thierry, J. E. Walker, and A. J. Wonacott. Mar. 24, 1977. *Nature.* vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society.* vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International.* vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature.* vol. 284, pp. 264-265.

Lim, Franklin and Anthony M. Sun. Nov. 21, 1980. "Microencapsulated Islets as Bioartificial Endocrine Pancreas." *Science.* vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters.* vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry.* vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science.* vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology.* vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature.* vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol.* vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta.* vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." *Chemistry Letters.* No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America.* vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters.* vol. 206, No. 2, pp. 262-266.

Mann, Stephen, John P. Hannington, and R. J. P. Williams. Dec. 11, 1986. "Phospholipid Vesicles as a Model System for Biomineralization." *Nature.* vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry.* vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research.* vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology.* vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology.* vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy.* New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research.* No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology.* vol. 107, pp. 743-751.

Cardin, Alan D. and H. J. R. Weintraub. Jan./Feb. 1989. "Molecular Modeling of Protein-Glycosaminoglycan Interactions." *Arteriosclerosis.* vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery.* vol. 71-B, No. 2, pp. 213-216.

Friedmann, Theodore. Jun. 16, 1989. "Progress Toward Human Gene Therapy." *Science.* vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America.* vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters.* vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual.* 2nd ed. New York: Cold Spring Harbor Laboratory Press. pp. 16.9-16.15.

Veis, A. 1989. "Biochemical Studies of Vertebrate Tooth Mineralization." *Biomineralization.* S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature.* vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery.* vol. 24, No. I, pp. 17-23.

Van de Pol, Frans C. M. Dec. 1990. "Thin-Film ZnO—Properties and Applications." *Ceramic Bulletin.* vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta.* vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research.* vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research.* vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry.* vol. 56, No. 22, pp. 14353-14358.

Jackson, David Y., David S. King, Jean Chmielewski, Sunil Singh, and Peter G. Schultz. 1991. "General Approach to the Synthesis of Short α-Helical Peptides." *Journal of the American Chemical Society.* vol. 113, pp. 9391-9392.

Polverini, Peter J., Noel P. Bouck, and Farzan Rastincjad. 1991. "Assay and Purification of Naturally Occurring Inhibitor of Angiogenesis." *Methods in Enzymology.* vol. 198, pp. 440-450.

Weiner, Stephen and Wolfie Traub. Feb. 1992. "Bone Structure: From Ångstroms to Microns." *The FASEB Journal.* vol. 6, pp. 879-885.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science.* vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research.* vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry.* vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society.* vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl.* vol. 31, pp. 709-726.

Stupp, Samuel I. And Glenn W. Ciegler. 1992. "Organoapatites: Materials for Artificial Bone. I. Synthesis and Microstructure." *Journal of Biomedical Materials Research.* vol. 26, pp. 169-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment" *Biochemistry.* vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America.* vol. 90, No. 8, pp. 3334-3338.

Langer, Robert and Joseph P. Vacanti. May 14, 1993. "Tissue Engineering." *Science.* vol. 260, No. 5110, pp. 920-926.

Mulligan, Richard C. May 14, 1993. "The Basic Science of Gene Therapy." *Science.* vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research.* vol. 72, No. 6, pp. 1005-1008.

Archibald, Douglas D. and Stephen Mann. Jul. 29, 1993. "Template Mineralization of Self-Assembled Anisotropic Lipid Microstructures." *Nature.* vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology.* vol. 150, No. 2, pp. 745-747.

Ross-Murphy, S. B. And K. P. Shatwell. May-Aug. 1993. "Polysaccharide Strong and Weak Gels." *Biorheology.* vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry.* vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater.* vol. 5, No. 10, pp. 1417-1423.

Fuhrhop, Jürgen-Hinrich, Dragon Spiroski, and Christoph Boettcher. 1993. "Molecular Monolayer Rods and Tubules Made of α-(L-Lysine),ω-(Amino) Bolaamphiphiles." *Journal of the American Chemical Society.* vol. 115, No. 4. pp. 1600-1601.

Graham, Stephan and Paul W. Brown. 1993. "The Low Temperature Formation of Octacalcium Phosphate." *Journal of Crystal Growth.* vol. 132, pp. 215-225.

Shimizu, Toshimi and Masakatsu Hato. 1993. "Self-Assembling Properties of Synthetic Peptidic Lipids." *Biochimica et Biophysica Acta.* vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research.* vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research.* vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials.* vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth.* vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research.* vol. 27 , pp. 1315 -1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology.* vol. 125, No. 5, pp. 1179-1188.

Ban, S., S. Maruno, H. lwata, and H. Itoh . 1994. "Calcium Phosphate Precipitation on the Surface of Ha-G-Ti Composite Under Physiologic Conditions." *Journal of Biomedical Materials Research.* vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials.* vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J.* vol. 302, pp. 175-179.

Klein, C. P. A. T., J. Ci. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research.* vol. 28, pp. 909-917.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials.* vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*, vol. 18, pp. 1417-1426.

Aletras, Alexios, Kleomenis Barlos, Dimitrios Gatos, Sophia Koutsogianni, and Petros Memos. 1995. "Preparation of the Very Acid-Sensitive Fmoc-Lys(Mtt)-OH." *International Journal of Peptide & Protein Research*. vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry*. vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996 "Nucleation and Inhibition of Hydroxyapatite Formation by Mineralized Tissue Proteins." *Biochem J*. vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Ratner, Buddy D., Allan S. Hoffman, Frederick J. Schoen, and Jack E. Lemons, Editors. 1996. *Biomaterials Science: An Introduction to Materials in Medicine*. San Diego, CA: Academic Press.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids*. vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature*. vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalie, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem*. vol. 7, No. 7, pp. 1135-1145.

Anderson, James M. And Matthew S. Shive. 1997. "Biodegradation and Biocompatibility of PLA and PLGA Microspheres." *Advanced Drug Delivery Reviews*. Vol. 28, pp. 5-24.

Draget, Kurt Inger, Gudmund Skjåk-Bræk, Olav Smidsrød. 1997. "Alginate Based New Materials." *International Journal of Biological Macromolecules.* vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function In Vitro Along Different Time Lines." *Journal of Biomedical Materials Research.* vol. 36, pp. 167-180.

Jaiswal, Neelarn, Stephen E. Haynesworth, Arnold I. Caplan, and Scott P. Bruder. 1997. "Osteogenic Differentiation of Purified, Culture-Expanded Human Mesenchymal Stem Cells In Vitro." *Journal of Cellular Biochemistry.* vol. 64, pp. 295-312.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.).* vol. 38, pp. 95-104.

Mann, Stephen. 1997. "Biomineralization: The Form(id)able Part of Bioinorganic Chemistry!" *J. Chem. Soc., Dalton Trans.* pp. 3953-3961.

Norrby, Klas. 1997. "Angiogenesis: New Aspects Relating to Its Initiation and Control." *APMIS.* Vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society.* vol. 119, No. 26, pp. 6209-6210, S2-S17.

Smith. George P. And Valery A. Petrenko. 1997. "Phage Display." *Chemical Reviews.* vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters.* pp. 443-444.

Weiner, Stephen and Lia Addadi. 1997. "Design Strategies in Mineralized Biological Materials." *J. Mater. Chem.* vol. 7. No. 5, pp. 689-702.

Wellings, Donald A. and Eric Atherton. 1997. "Standard Film Protocols." *Methods in Enzymology.* vol. 289, pp. 44-67.

Wen, H. B., J. G. C. Wollte, J. R. de Wijn, Q. Liu, F. Z. Cui, and K. de Groot. 1997. "Fast Precipitation of Calcium Phosphate Layers on Titanium Induced by Simple Chemical Treatments." *Biomaterials.* vol. 18, No. 22, pp. 1471-1478.

Yu, Ying-Ching. Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology.* vol. 289, pp. 571-587.

Zhitomirsky, I. and L. Gal-Or. 1997. "Electrophoretic Deposition of Hydroxyapatite." *Journal of Materials Science: Materials in Medicine.* pp. 213-219.

Veis, Arthur, Kuiru Wei, Charles Sfeir, Anne George, and James Malone. Jan. 1998. "Properties of the (DSS) Triplet Repeat Domain of Rat Dentin Phosphophoryn." *European Journal of Oral Sciences.* vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery.* vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research.* vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science.* vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery.* vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society.* vol. 120, No. 39, pp. 9979-9987.

Borkenhagen, M., J.-F. Clémence, Fl Sigrist, and P. Aebischer. 1998. "Three-Dimensional Extracellular Matrix Engineering in the Nervous System." *Journal of Biomedical Materials Research.* vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.).* vol. 43, pp. 380-398.

Fields, Gregg B., Janelle L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science).* vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences.* vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research.* vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering.* vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir.* vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valylvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research.* vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research.* vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials.* vol. 19, pp. 2031-2043.

Weiner, S. And H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research.* vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.).* vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research.* vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir.* vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society.* vol. 120, No. 46, pp. 11977-11985.

Yamada, Norihiro, Katsuhiko Ariga, Masanobu Naito, Kazuhiro Matsubara, and Emiko Koyama. 1998 "Regulation of β-Sheet Structures Within Amyloid-Like β-Sheet Assemblage from Tripeptide Derivatives." *Journal of the American Chemical Society.* vol. 120, No. 47, pp.12192-12199.

Chusuei, Charles C., D. Wayne Goodman, Michael J. Van Stipdonk, Dina R. Justes, and Emile A. Schweikert, Jan. 1, 1999. "Calcium Phosphate Phase Identification Using XPS and Time-of-Flight Cluster SIMS." *Analytical Chemistry.* vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science.* vol. 283, pp. 523-526.

Won, You-Yeon, H. Ted Davis, and Frank S. Bates. Feb. 12, 1999. "Giant Wormlike Rubber Micelles." *Science.* vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering.* vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters.* vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature.* vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science.* vol. 284, pp. 489-493.

Hahn, Jungseok and Stephen E. Webber. Apr. 1999. "Modification of Surfaces by Covalent Attachment of Polymer Micelles." *Macromolecular Symposia.* vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience.* vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology.* Invited Paper BI-WeM7.

McDonald, John W., Xiao-Thong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine.* vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater.* vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin.* vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery.* vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine.* vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physiol. Endocrinol. Metab.* vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir.* vol. 15, No. 16, pp. 5212-5218.

Fields, Gregg B. 1999. "Induction of Protein-like Molecular Architecture by Self-Assembly Processes." *Bioorganic & Medicinal Chemistry.* vol. 7, pp. 75-81.

Haynes, Andrew J., Wei-Qun Huang, Jamie Mallah, Dajun Yang, Marc E. Lippman, and Lu-Yuan Li. 1999. "Angiopoietin-I and Its Receptor Tie-2 Participate in the Regulation of Capillary-like Tubule Formation and Survival of Endothelial Cells." *Microvascular Research.* vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research.* vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials.* vol. 20, pp. 809-816.

Lee, Kevin J. and Thomas M. Jessell. 1999. "The Specification of Dorsal Cell Fates in the Vertebrate Central Nervous System." *Annual Review of Neuroscience.* vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir.* vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth.* vol. 206, pp. 308-321.

Miyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials.* vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials.* vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science.* vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir.* vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials.* vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem.* vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine.* vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research.* vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine.* vol. 10, pp. 401-409.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry.* vol. 38, No. 5, pp. 1659-1668.

Huq, N. Laila, Keith J. Cross, and Eric C. Reynolds. Feb. 4 2000. "Molecular Modelling of a Multiphosphorylated Sequence Motif Bound to Hydroxyapatite Surfaces." *Journal of Molecular Modeling.* vol. 6, pp. 35-47.

Martinez, J. S., G. P. Zhang, P. D. Holt, H.—T. Jung, C. J. Carrano, M. G. Haygood, and Alison Butler. Feb. 18, 2000. "Self-Assembling Amphiphilic Siderophores from Marine Bacteria." *Science.* vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry.* vol. 275, No. 11, pp. 7701-7707.

Cao. H., J. Y. Xu, E. W. Seelig, and R. P. H. Chang. May 22, 2000. "Microlaser Made of Disordered Media." *Applied Physics Letters.* vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery.* vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America.* vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature.* vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry.* vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science.* vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell.* vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters.* vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America.* vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science.* vol. 9, pp. 1095-1105.

Archer, Eric A., Noah T. Goldberg, Vincent Lynch, and Michael J. Krische. 2000. "Nanostructured Polymer Duplexes via the Covalent Casting of I-Dimensional H-Bonding Motifs: A New Strategy for the Self-Assembly of Macromolecular Precursors." *Journal of the American Chemical Society.* vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir.* vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology.* vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules.* vol. 1, No. 4, pp. 752-756.

Bourel, Line, Olivier Canon, Hélène Gras-Masse, and Oleg Melnyk. 2000. "The Deprotection of Lys(Mtt) Revisited." *Journal of Peptide Science.* vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules.* vol. 1, No. 4, pp. 627-631.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun.* pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research.* vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research.* vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research.* vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains." *Biopolymers.* vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects.* vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel β-Sheet Network." *Biochimica et Biophysica Acta.* vol. 1475, pp. 346-352.

Langer, Robert. 2000. "Biomaterials in Drug Delivery and Tissue Engineering: One Laboratory's Experience." *Accounts of Chemical Research.* vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med.* vol. 136, No. 2, pp. 100-109.

Lu, Lichun, Susan J. Peter, Michelle D. Lyman, Hui-Lin Lai, Susan M. Leite, Janet A. Tamada, Shim Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials.* vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials.* vol. 21, pp. 1121-1127.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research.* vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman.

2000. "Neural Cell Response to Multiple Novel Sites on Laminin-1." *Journal of Neuroscience Research.* vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release.* vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release.* vol. 65, pp. 389-402.

Thareja, R. K. And a. Mitra. 2000. "Random Laser Action in ZnO." *Appl. Phys.* vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique.* vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research.* vol. 49, pp. 345-352.

Yamada, Norihiro and Katsuhiko Ariga. 2000. "Formation of β-Sheet Assemblage with a View to Developing an Amyloid Model." *Synlett.* vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science.* vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000, "Hydrophilicity of Polar and Apolar Domains of Amphiphiles." *Journal of Colloid and Interface Science.* vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research.* vol. 59, pp. 312-320.

Orlic, Donald, Jan Kajstura, Stefano Chimenti, Igor Jakonuk, Stacie M. Anderson, Baosheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature.* vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation.* vol. 81, No. 4, pp. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res.* vol. 16, No. 5, pp. 1508-1519.

Rabchevsky, Alexander G. and George M. Smith. May 2001. "Therapeutic Interventions Following Mammalian Spinal Cord Injury." *Arch. Neurol.* vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science.* vol. 292, pp. 1897-1899.

Lee, Kuen Yong and David J. Mooney. Jul. 2001. "Hydrogels for Tissue Engineering." *Chemical Reviews.* vol. 101, No. 7, pp. 1869-1879.

Aggeli, A., I. A. Nyrkova, M. Bell, R. Harding, L. Carrick, T. C. B. McLeish, A. N. Semenov, and N. Roden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America.* vol. 98, No. 21, pp. 11857-11862.

Hartgerink, Jeffrey D., Elia Beniash, and Samuel I. Stupp. Nov. 23, 2001. "Self-Assembly and Mineralization of Peptide-Amphiphile Nanofibers." *Science.* vol. 294, pp. 1684-1688.

Richardson, Thomas P., Martin C. Peters, Alessandra B. Ennett, and David J. Mooney. Nov. 2001. "Polymeric System for Dual Growth Factor Delivery." *Nature Biotechnology.* vol. 19, pp. 1029-1034.

Mathew, Mathai and Shozo Takagi. Nov.-Dec. 2001. "Structures of Biological Minerals in Dental Research." *Journal of Research of the National Institute of Standards and Technology.* vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research.* vol. 18, No. 12, pp. 1747-1753.

Barrére, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine,* vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir.* vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science.* vol. 36, pp. 3253-3260.

Chang, John C., Gregory J. Brewer, and Bruce C. Wheeler. 2001. "Modulation of Neural Network Activity by Patterning." *Biosensors & Bioelectronics.* vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research.* vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal.* vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir.* vol. 17, No. 17, pp. 5352-5360.

Hoess, Ronald H. 2001. "Protein Design and Phage Display." *Chemical Reviews.* vol. 101, No. 10, pp. 3205-3218.

Huang, Eric J. and Louis F. Reichardt. 2001. "Neurotrophins: Roles in Neuronal Development and Function." *Annual Review of Neuroscience.* vol. 24, pp. 677-736.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials.* vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and Its Biological Reaction in Vivo." *Biomaterials.* vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research.* vol. 57, pp. 327-335.

Look, D. C. 2001. "Recent Advances in ZnO Materials and Devices." *Materials Science and Engineering.* vol. B80, pp. 383-387.

Matsui, Hiroshi, and Gary E. Douberly, Jr. 2001. "Organization of Peptide Nanotubes into Macroscopic Bundles." *Langmuir.* vol. 17, No. 25, pp. 7918-7922.

Neet, K. E. and R. B. Campenot. 2001. "Receptor Binding, Internalization, and Retrograde Transport of Neurotrophic Factors." *CMLS, Cell Mol. Life Sci.* vol. 58, pp. 1021-1035.

Otsuka, Hidenori, Yukio Nagasaki, and Kazunori Kataoka. 2001. "Self-Assembly of Poly(ethylene glycol) -based Block Copolymers for Biomedical Applications." *Current Opinion in Colloid & Interface Science.* vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,107-Nucleobase Bolaamphiphiles." *Journal of the American Chemical Society.* vol. 123, No. 25, pp. 5947-5955, S1-S16.

Socrates, George. 2001. *Infrared and Raman Characteristic Group Frequencies: Tables and Charts.* Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir.* vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research.* vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research.* vol. 56, pp. 216-221.

Torchilin, Vladimir P. 2001. "Structure and Design of Polymeric Surfactant-Based Drug Delivery Systems." *Journal of Controlled Release.*vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters.* vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society.* vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-62 Induction of Smooth Muscle Cell Phenotype Requires Transcriptional and Post-transcriptional Control of Serum Response Factor." *The Journal of Biological Chemistry.* vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal.* vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials.* vol. 14, No. 3, pp. 198-203.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America.* vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature.* vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America.* vol. 99, No. 8, pp. 5133-5138.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America.* vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature.* vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature.* vol. 417, pp. 547-551.

Storch, Alexander and Johannes Schwarz. May 2002. "Neural Stem Cells and Neurodegeneration." *Current Opinion in Investigational Drugs.* vol. 3, No. 5, pp. 774-781.

Lendlein, Andreas and Robert Langer. May 31, 2002. "Biodegradable, Elastic Shape-Memory Polymers for Potential Biomedical Applications." *Science.* vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron.* vol. 34, pp. 895-903.

Catledge, Shane A., Marc D. Fries, Yogesh K. Vohra, William R. Lacefield, Jack E. Lemons, Shanna Woodard, and Ramakrisluut Venugopalan. Jun.-Aug. 2002. "Nanostructured Ceramics for Biomedical Implants." *Journal of Nanoscience and Nanotechnology.* vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Scioences of the United States of America.* vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering.* vol. 8, No. 5, pp. 753-761.

Chang, Hua, Chester W. Brown, and Martin M. Matzuk. Dec. 2002. "Genetic Analysis of the Mammalian Transforming Growth Factor-β Superfamily." *Endocrine Reviews.* vol. 23, No. 6, pp. 787-823.

Busqué, Félix, Stephanie a. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem.* vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn.* vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials.* vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience.* vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience.* vol. 20, pp. 140-153.

Costa, Silvia, Thierry Planchenault, Cecile Charriere-Bertrand, Yann Mouchel, Christiane Fages, Sharon Juliano, Thierry Lefrancois, Georgia Barlovatz-Meirnon, and Marcienne Tardy. 2002. "Astroglial Permissivity for Neuritic Outgrowth in Neuron-Astrocyte Cocultures Depends on Regulation of Laminin Bioavailability." *GLIA.* vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem.* vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from Its CD Spectrum?" *Journal of the American Chemical Society.* vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research.* vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir.* vol. 18, No. 1, pp. 252-258.

Issac, Roy and Jean Chmielewski. 2002. "Approaching Exponential Growth with a Self-Replicating Peptide." *Journal of the American Chemical Society.* vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part I. Clip Design, Behavioral Outcomes, and Histopathology." *Journal of Neurotrauma.* vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma.* vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun.* pp. 2092-2093.

Lauer, L., A. Vogt, C. K. Yeung, W. Knoll, and A. Offenhausser. 2002. "Electrophysiological Recordings of Patterned Rat Brain Stem Slice Neurons." *Biomaterials.* vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols.* vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters.* vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem.* vol. 13, No. 3, pp. 510-517.

Okano, Hideyuki. 2002. "Stem Cell Biology of the Central Nervous System." *Journal of Neuroscience Research.* vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience.* vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials.* vol. 23, pp. 725-733.

Rowley, Jon A. and David J. Mooney. 2002. "Alginate Type and RGD Density Control Myoblast Phenotype." *Journal of Biomedical Materials Research.* vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science.* vol. 7, pp. 262-266.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics.* vol. 17, pp. 87-93.

Tryoen-Tth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research.* vol. 60, pp. 657-667.

Young, Wise. 2002. "Spinal Cord Contusion Models." *Progress in Brain Research.* vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology.* vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery.* vol. 14, No. 3, pp. 308-316.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery.* vol. 85-A, No. 8, pp. 1544-1552, 141.

Pavlov, Georges, Stéphanie Finet, Karine Tatarenko, Evgueniya Komeeva, and Christine Ebel. 2003. "Conformation of Heparin Studied with Macromolecular Hydrodynamic Methods and X-ray Scattering." *Eur. Biophys. J.* vol. 32, pp. 437-449.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery.* vol. 85-A, No. 10, pp. 1927-1935.

Zhang, Shuguang. Oct. 2003. "Fabrication of Novel Biomaterials Through Molecular Self-Assembly." *Nature Biotechnology.* vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society.* vol. 125, No. 32, pp. 9619-9628.

Alsina, Jordi and Fernando Albericio. 2003. "Solid-Phase Synthesis of C-Terminal Modified Peptides." *Biopolymers (Peptide Science).* vol. 71, pp. 454-477.

Boontheekul, Tanyarut and David J. Mooney. 2003. "Protein-Based Signaling Systems in Tissue Engineering." *Current Opinion in Biotechnology.* vol. 14, pp. 559-565.

Fauza, Dario O. 2003. "Tissue Engineering: Current State of Clinical Application." *Current Opinion in Pediatrics.* vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers.* vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers.* vol. 70, pp. 346-354.

Gergely, C. S., P. Bar Yosef. R. Govrin-Lippman, F. Cuisinier, and H. Fëredi-Milhofer. 2003. "The Deposition of Calcium Phosphates Within Polyelectrolyte Multilayer Films." *Key Engineering Materials.* vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules.* vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira as Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research.* vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules.* vol. 4, No. 3, pp. 518-528.

Niece, Krista L., Jeffrey D. Haftgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society.* vol. 125, No. 24, pp. 7146-7147.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology.* vol. 459, pp. 1-8.

Wu, Sufan, Yoshihisa Suzuki, Yoko Ejiri, Toru Noda, Hongliang Bai, Masaaki Kitada, Kazuya Kataoka, Masayoshi Ohta, Hirotorni Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research.* vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed.* vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society.* vol. 125, No. 45, pp. 13680-13681.

Hirano, Yoshiaki and David J. Mooney. Jan. 5, 2004. "Peptide and Protein Presenting Materials for Tissue Engineering." *Advanced Materials.* vol. 16, No. 1, pp. 17-25.

Silva, Gabriel a., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting*. Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8786-8790.

Pearse, Damien D., Francisco C. Pereira, Alexander E. Marcillo, Margaret L. Bates, Yerko a. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J.* vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets*. vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters*. vol. 5, No. 2, pp. 249-252.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Clemetson, K. J., and J. M. Clemetson. 1998. "Integrins and Cardiovascular Disease." *CMLS Cellular and Molecular Life Sciences*. vol. 54, pp. 502-513.

Dupin, Elisabeth, and Nicole M. Le Douarin. 2003. "Development of Melanocyte Precursors from the Vertebrate Neural Crest." *Oncogene*. vol. 22, pp. 3016-3023.

Mardilovich, Anastasia, and Efrosini Kokkoli. 2004. "Biomimetic Peptide—Amphiphiles for Functional Biomaterials: The Role of GRGDSP and PHSRN." *Biomacromolecules*. vol. 5, No. 3, pp. 950-957.

Cui, Honggang, Takahiro Muraoka, Andrew G. Cheetham, and Samuel I. Stupp. 2009. "Self-Assembly of Giant Peptide Nanobelts." *Nano Letters*. vol. 9, No. 3, pp. 945-951.

Tam, James P. 1996. "Recent Advances in Multiple Antigen Peptides." Journal of Immunological Methods. vol. 196, pp. 17-32.

Merkler, Doron, Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." The Journal of Neuroscience. vol. 21, No. 10, pp. 3665-3673.

Bonnet, Dominique, Kader Thiam, Estelle Loing, Oleg Melnyk, and Hélène Gras-Masse. 2001. Synthesis by Chemoselective Ligation and Biological Evaluation of Novel Cell-Permeable PKC-ζ Pseudosubstrate Lipopeptides. J. Med. Chem. vol. 44, No. 3, pp. 468-471.

Grothe, Claudia and Guido Nikkhah. 2001. "The role of Basic Fibroblast Growth Factor in Peripheral Nerve Regeneration." Anat. Embryol. vol. 204, pp. 171-177.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That Is Induced to Self-Assemble Under Physiological Conditions." Biosis. Society for Neuroscience Abstract Viewer and Itinerary Planner—2002. Abstract No. 825.4. 32nd Annual Meeting of the Society for Neuroscience; Orlando, Florida.

Leng, J., S. U. Egelhaaf, and M. E. Cates. Sep. 2003. "Kinetics of the Micelle-to-Vesicle Transition: Aqueous Lecithin-Bile Salt Mixtures." Biophysical Journal. vol. 85, No. 3, pp. 1624-1646.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similair Activities to the All-L-Peptide in Vitro and in Vivo." The Journal of Biological Chemistry. vol. 267, No. 20, pp. 14118-14121.

Margomenou-Leonidopoulou, G. 1994. "Thermotropic Mesophases of Ionic Amphiphiles. II. Ionic Amphiphiles in Aqueous Media." Journal of Thermal Analysis. vol. 42, pp. 1041-1061.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Goveas, J. L. and S. T. Milner. 1997. "Dynamics of the Lamellar—Cylindrical Transition in Weekly Segregated Diblock Copolymer Melts." Macromolecules. vol. 30, No. 9, pp. 2605-2612.

Munson, John B. and Stephen B. McMahon. 1997. "Effects of GDNF on Axotomized Sensory and Motor Neurons in Adults Rats." European Journal of Neuroscience. vol. 9, pp. 1126-1129.

Fernandez, A., M. A. Alsina, I. Haro, R. Galantai, and F. Reig. 1998. "Synthesis and Physicochemical Characterization of Cyclic Laminin Related Petides," Langmuir vol. 14, No. 13, pp. 3625-3630.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." Chem. Commun. pp. 1687-1688.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann. 2001. "Selective Adhesion of Endothelial Cells to Artificial Membranes with a Synthetic RGD-Lipopeptide." Chem. Eur. J. vol. 7, No. 5, pp. 1095-1101.

Blight, Andrew R. Nov. 2002. "Miracles and Molecules—Progress in Spinal Cord Repair." Nature Neuroscience Supplement. vol. 5, pp. 1051-1054.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon, 2002. "Flow Oriented Linear Dichroism to Probe Protein Orientation in Membrane Environments." Phys. Chem. Chem. Phys. vol. 4, pp. 4051-4057.

Silva, G. A., K. L. Kahl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fermentans." Eur. J. Blochem. vol. 270, pp. 3271-3279.

Czeisler, C., V. M. Tysseling-Mattiace, G. A. Silva, S. I. Stupp, and J. A. Kessler. 2003. "Behavoral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. Page 1. http://sfn.scholarone.com/itin2003/main.html?new_page_id=126&abstract_&1554 . . . .

Schmidt, Christine E. and Jennie Baier Leach. 2003. "Neural Tissue Engineering: Strategies for Repair and Regeneration." Annu. Rev. Blomed. Eng. vol. 5. pp. 293-347.

t' Hart, Bert A. and Sandra Amor, 2003. "The Use of Animal Models to Investigate the Pathogenesis of Neuroinflammatory Disorders of the Central Nervous System." Current Opinion in Neurology. vol. 16, pp. 375-383.

Beniash, Ella, Jeffery D. Hartgerink, Hannah Storrie, John C. Stendahl, and Samuel I. Stupp. 2005. "Self-Assembling Peptide Amphiphile Nanofiber Matrices for Cell Entrapment." Acta Biomaterialia. vol. 1, pp. 387-397.

Hoke, Ahmet. Aug. 2006. "Mechanisms of Disease: What Factors Limit the Success of Peripheral Nerve Regeneration in Humans?" Nature Clinical Practice Neurology. vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1016-1024.

The LabRat.com. 2007, updated. Hank's Buffered Salt Solution (HBSS) Recipe. http://www.thelabrat.com/protocolsHanks.shtml. Printed Jan.19, 2007. pp. 1-2.

Copping, Aaron M. And Vanda R. G. Pond. Dec. 9, 1950. "Folic Acid as a Growth-Factor for the Rat" Nature. No. 4232, p. 993.

Mulloy, Barbara and Mark J. Forster. 2000. "Conformation and Dynamics of Heparin and Heparan Sulfate." Glycobiology. vol. 10, No. 11, pp. 1147-1156.

Bruggeman, Holger, Sebastian Baumer, Wolfgang Florian Fricke, Arnim Wiezer, Heiko Liesegang, lwona Decker, Christina Herzberg, Rosa Martinez-Arias, Rainer Merkl, Anke Henne, and Gerhard Gottschalk. Feb. 4, 2003. "The Genome Sequence of Clostridium tetani, the Causative Agent of Tetanus Disease." PNAS. vol. 100, No. 3, pp. 1316-1321.

Invitrogen. Printed Jan. 22, 2008. "Dulbecco's Modified Eagle Medium (D-MEM) (1X) Liquid (High Glucose)." http://www.invitrogen.com/content.cfm?pageld=95&fuseaction=MediaForm. dsp_mediaFomn&productld... .

Uniprot entry for Q899Z6. Printed Mar. 14, 2008. http://www.pir.uniprot.org/cgi-bin/upEntry?id=Q899Z6_CLOTE. 3 pages.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." Cancer Research. vol. 53, pp. 3459-3461.

Jin, Young-Gu and K. J. Chang. Feb. 26, 2001. "Mechanism for the Enhanced Diffusion of Charged Oxygen Ions in $SiO_2$." Physical Review Letters. vol. 86, No. 9, pp. 1793-1796.

Matsui, Hiroshi and Robert MacCuspie. Dec. 2001. "Metalloporphyrin Nanotube Fabrication Using Peptide Nanotubes as Templates." Nano Letters. vol. 1, No. 12, pp. 671-675.

Irvine, Darrell J. and Anne M. Mayes. 2001. "Nanoscale Clustering of RGD Peptides at Surfaces Using Comb Polymers. 1. Synthesis and Characterization of Comb Thin Films." Biomacromolecules. vol. 2, No. 1, pp. 85-94.

Matsui, Hiroshi, Precila Porrata, and Gary E. Douberly, Jr. 2001. "Protein Tubule Immobilization on Self-Assembled Monolayers on Au Substrates." Nano Letters. vol. 1, No. 9, pp. 461-464.

Slocik, Joseph M., Joshua T. Moore, and David W. Wright. Mar. 2002. Monoclonal Antibody Recognition of Histidine-Rich Peptide Encapsulated Nanoclusters. Nano Letters. vol. 2, No. 3, pp. 169-173.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." Langmuir. vol. 18, No. 8, pp. 3332-3335.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." Nano Letters. vol. 2, No. 6, pp. 583-587.

"AccessScience Search Results. Amphiphile." Accessed online May 7, 2007. http://www.accessscience.com/search/ asearch?location=titlestext&newSearch=l&pubpriv=private&categories=dictionary&categval=dictionary&text=amphiphile. McGraw-Hill Encyclopedia of Science & Technology Online.

Kibbey, Maura C., Mathias Jucker, Benjamin S. Weeks, Rachael L. Neve, Wiliam E. Van Nostrand, and Hynda K. Kleinman. Nov. 1993. "β-Amyloid Precursor Protein Binds to the Neurite-Promoting IKVAV Site of Laminin." Proc. Natl. Acad. Sci. U.S.A. vol. 90, pp. 10150-10153.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgery." Neurosurgery Online. vol. 38, No. 4, pp. 733-736.

Rapaport, Hanna, Kristian Kjaer, Torben R. Jensen, Leslie Leiserowitz, and David A. Tirrell. 2000. "Two-Dimensional Order in β-Sheet Peptide Monolayers." Journal of the American Chemical Society. vol. 122, No. 50, pp. 12523-12529.

Avrahami, Dorit and Yechiel Shai. 2002. "Conjugation of a Magainin Analogue with Lipophilic Acids Controls Hydrophobicity, Solution Assembly, and Cell Selectivity." Biochemistry. vol. 41, No. 7, pp. 2254-2263.

Yamada, Masanori, Yuichi Kadoya, Shingo Kasai, Kozue Kato, Mayumi Mochizuki, Norio Nishi, Nobuhisa Watanabe, Hynda K. Kleinman, Yoshihiko Yamada, and Motoyoshi Nomizu. 2002. "Ile-Lys-Val-Ala-Val (IKVAV)-Containing Laminin α1 Chain Peptides Form Amyloid-like Fibrils." FEBS Letters. vol. 530, pp. 48-52.

McGregor,Clare-Louise, Lu Chen, Neil C. Pomroy, Peter Hwang, Sandy Go, Avijit Chakrabartty, and Gilbert G. Privé. Feb. 2003. "Lipopeptide Detergents Designed for the Structural Study of Membrane Proteins." Nature Biotechnology. vol. 21, pp. 171-176.

Ohmori, Hideya, Yasumitsu Sato, and Akiyoshi Namiki. 2004. "The Anticonvulsant Action of Propofol on Epileptiform Activity in Rat Hippocampal Slices." Anesth. Analg. vol. 99, pp. 1095-1101.

Shahraki, Ali and Trevor W. Stone. 2004. "Blockade of Presynaptic Adenosine Al Receptor Responses by Nitric Oxide and Superoxide in Rat Hippocampus." European Journal of Neuroscience. vol. 20, pp. 719-728.

Sone, Eli D. and Samuel I. Stupp. 2004. "Semiconductor-Encapsulated Peptide-Amphiphile Nanofibers." Journal of the American Chemical Society. vol. 126, No. 40, pp. 12756-12757.

Smith, L. A. and P. X. Ma. 2004. "Nano-Fibrous Scaffolds for Tissue Engineering." Colloids and Surfaces. B: Biointerfaces. vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures." J. Phys. Chem. B. vol. 108, No. 26, pp. 8817-8822.

Tsonchev, Stefan, Alessandro Troisi, George C. Schatz, and Mark A. Ratner. 2004. "All-Atom Numerical Studies of Self-Assembly of Zwitterionic Peptide Amphiphiles." J. Phys. Chem. B. vol. 108, No. 39, pp. 15278-15284.

Tsonchev, Stefan, Alessandro Troisi, George C. Schatz, and Mark A. Ratner. 2004. "On the Structure and Stability of Self-Assembled Zwitterionic Peptide Amphiphiles: A Theoretical Study." Nano Letters. vol. 4, No. 3, pp. 427-431.

Arnold, Michael S., Mustafa O. Guler, Mark C. Hersam, and Samuel I. Stupp. 2005. "Encapsulation of Carbon Nanotubes by Self-Assembling Peptide Amphiphiles." Langmuir. vol. 21, No. 10, pp. 4705-4709.

Behanna, Heather A., Jack J. J. M. Donners, Alex C. Gordon, and Samuel I. Stupp. 2005. "Coassembly of Amphiphiles with Opposite Peptide Polarities into Nanofibers." Journal of the American Chemical Society. vol. 127, No. 4, pp. 1193-1200.

Bitton, Ronit, Judith Schmidt, Markus Biesalski, Raymond Tu, Matthew Tirrell, and Havazelet Bianco-Peled. 2005. "Self-Assembly of Model DNA-Binding Peptide Aniphiphiles." Langmuir. vol. 21, No. 25, pp. 11888-11895.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." Bioconjugate Chem. vol. 16, No. 6, pp. 1343-1348.

de Loos, Maaike, Ben L. Feringa, and Jan H. van Esch. 2005. "Design and Application of Self-Assembled Low Molecular Weight Hydrogels." Eur. J. Org. Chem. pp. 3615-3631.

Guler, Mustafa O., Randal C. Claussen, and Samuel I. Stupp. 2005. "Encapsulation of Pyrene Within Self-Assembled Peptide Amphiphile Nanofibers." Journal of Materials Chemistry. vol. 15, pp. 4507-4512.

Guler, Mustafa O., Jonathan K. Pokorski, Daniel H. Appella, and Samuel I. Supp. 2005. "Enhanced Oligonucleotide Binding to Self-Assembled Nanofibers." Bioconjugate Chem. vol. 16, No. 3, pp. 501-503.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Adv. Mater. vol. 17, pp. 2612-2617.

Silva, Gabriel A. 2005. "Nanotechnology Approaches for the Regeneration and Neuroprotection of the Central Nervous System." Surgical Neurology. vol. 63, pp. 301-306.

Silva, Gabriel A. 2005. "Small Neuroscience: The Nanostructure of the Central Nervous System and Emerging Nanotechnology Applications." Current Nanoscience. vol. 1, No. 3, pp. 225-236.

Solis., F. J. S. I. Stupp, and M. Olvera de la Cruz. 2005. "Charge Induced Pattern Formation on Surfaces: Segregation in Cylindrical Micelles of Cationic-Anionic Peptide-Amphiphiles." The Journal of Chemical Physics. vol. 122, No. 5, 054905-1-054905-9.

Tovar, John D., Randal C. Claussen, and Samuel I. Stupp. 2005. "Probing the Interior of Peptide Amphiphile Supramolecular Aggregates." Journal of the American Chemical Society. vol. 127, No. 20, pp. 7337-7345.

Hosseinkhani, Hossein, Mohsen Hosseinkhani, and Hisatoshi Kobayashi. Jul. 2006. "Design of Tissue-Engineered Nanoscaffold Through Self-Assembly of Peptide Amphiphile." Journal of Bioactive and Compatible Polymers. vol. 21, No. 4, pp. 277-296.

Engler, Adam J., Shamik Sen, H. Lee Sweeney, and Dennis E. Discher. Aug. 25, 2006. "Matrix Elasticity Directs Stem Cell Lineage Specification." Cell. vol. 126, pp. 677-689.

Brunsveld, L., J. Kuhlmann, and H. Waldmann. 2006. "Synthesis of Palmitoylated Ras-Peptides and -Proteins." Methods. vol. 40, pp. 151-165.

Elgersma, Ronald C., Tania Meijneke, Remco de Jong, Arwin J. Brouwer, George Posthuma, Dirk T. S. Rijkers, and Rob M. J. Liskamp. 2006. "Synthesis and Structural Investigations of N-alkylated β-peptidosulfonamide-peptide Hybrids of the Amyloidogenic Amylin(20-29) Sequence: Implications of Supramolecular Folding for the Design of Peptide-Based Bionanomaterials." Organic & Biomolecular Chemistry. vol. 4, pp. 3587-3597.

Guler, Mustafa O., Lorraine Hsu, Stephen Soukasene, Daniel A. Harrington, James F. Hulvat, and Samuel I. Stupp. 2006. "Presentation of RGDS Epitopes on Self-Assembled Nanofibers of Branched Peptide Amphiphiles." Biomacromolecules. vol. 7, No. 6, pp. 1855-1863.

Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." Journal of Biomedical Materials Research Part A. pp. 157-167.

Hosseinkhani, Hossein, Mohsen Hosseinkhani, Ali Khademhosseini, Hisatoshi Kobayashi, and Yasuhiko Tabata. 2006. "Enhanced Angiogenesis Through Controlled Release of Basic Fibroblast Growth Factor from Peptide Amphiphile for Tissue Regeneration." Biomaterials. vol. 27, pp. 5836-5844.

Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." Langmuir. vol. 22, No. 7, pp. 3259-3264.

Paramonov, Sergey E., Ho-Wook Jun, and Jeffrey D. Hartgerink. 2006. "Self-Assembly of Peptide-Amphiphile Nanofibers: The Roles of Hydrogen Bonding and Amphiphilic Packing." Journal of the American Chemical Society. vol. 128, No. 22, pp. 7291-7298.

Rajangam, Kanya, Heather A. Behanna, Michael J. Hui, Xiaoqiang Han, James F. Hulvat, Jon W. Lomasney, and Samuel I. Stupp. 2006. "Heparin Binding Nanostructures to Promote Growth of Blood Vessels." Nano Letters. vol. 6, No. 9, pp. 2086-2090.

Reches, Meital and Ehud Gazit. 2006. "Molecular Self-Assembly of Peptide Nanostructures: Mechanism of Association and Potential Uses." Current Nanoscience. vol. 2, No. 2, pp. 105-111.

Stendahl, John C., Mukti S. Rao, Mustafa O. Guler, and Samuel I. Stupp. 2006. "Intermolecular Forces in the Self-Assembly of Peptide Amphiphile Nanofibers." Advanced Functional Materials. vol. 16, pp. 499-508.

Behanna, Heather A., Kanya Rajangam, and Samuel I. Stupp. 2007. "Modulation of Fluorescence Through Coassembly of Molecules in Organic Nanostructures." Journal of the American Chemical Society. vol. 129, No. 2, pp. 321-327.

Meijer, Joris T., Marjolijn Roeters, Valentina Viola, Dennis W. P. M. Löwik, Gert Vriend, and Jan C. M. van Hest. 2007. "Stabilization of Peptide Fibrils by Hydrophobic Interaction." Langmuir. vol. 23, No. 4, pp. 2058-2063.

Jackowski, Andre. 1995. "Neural Injury Repair: Hope for the Future as Barriers to Effective CNS Regeneration Become Clearer." J. Neurosurg. vol. 9, pp. 303-317.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." Langmuir. vol. 21, No. 3, pp. 1001-1008.

Anthony, Shawn G. 2003. "Injectable Biomaterials for Bone Tissue Engineering." http://www.nuance.northwestern. edu/downloads/Anthony%20Murphy%20Report%20Spring%202003.pdf.

* cited by examiner

*Primary Examiner*—David Lukton

(57) ABSTRACT

The present invention provides for bola amphiphiles compositions which have more than one lyophilic (hydrophilic) head group and a hydrophobic (hydrophobic) moiety capable of hydrogen bonding with other bola amphiphiles. These bola amphiphiles are capable of self assembling into micelles. The advantage of these bola amphiphiles is that they may self-assemble into micelles whose lyophilic head groups are located within the core and on the surface of the micelles. The lyophilic environment at the core and on the surface of the micelles may be different and may be controlled by the choice of head group moieties on the bola amphiphiles. The utility of these compositions is that they can be used to load or encapsulate polar drugs, DNA, mineralizable inorganic salts, or other molecules of interest within the polar interior of the micelle. Such compositions may also provide small water-filled ion-conducting channels within their structure suitable for use in micro electromechanical devices, as templates for nanowires or dielectrics, and as chemical sensors.

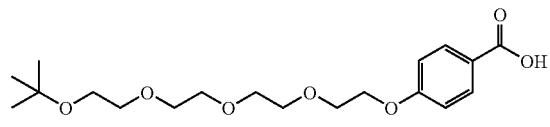
14
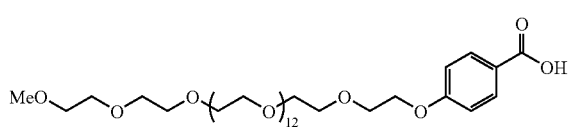
15
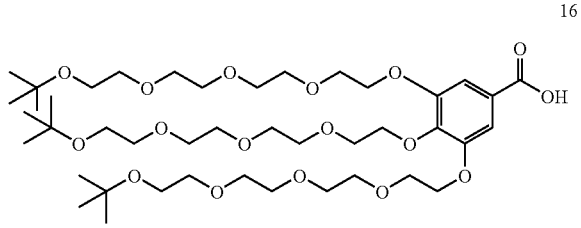
16
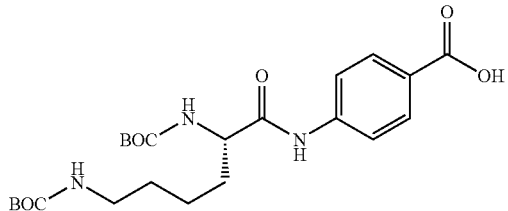
17
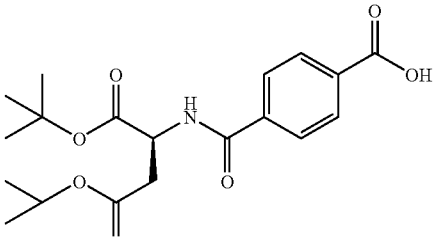
18
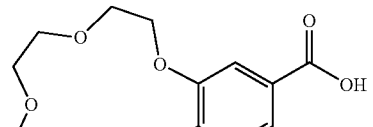
19
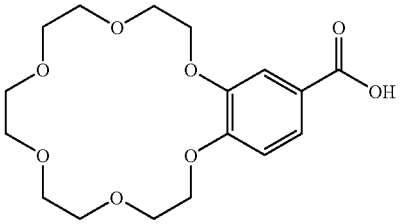
20
20 Claims, 14 Drawing Sheets

14

15

16

17

18

19

20

US 7,683,025 B2

SYNTHESIS AND SELF-ASSEMBLY OF ABC TRIBLOCK BOLA PEPTIDE AMPHIPHILES

CROSS REFERENCE TO RELATED APPLICATIONS

This application claims the benefit of U.S. Provisional Application No. 60/425,536 filed Nov. 12, 2002, entitled SELF ASSEMBLY OF MULTI-DIMENSIONAL PEPTIDE AMPHIPHILES and the benefit of U.S. Provisional Application No. 60/425,689 filed Nov. 12, 2002

GOVERNMENT INTEREST

The United States Government may have certain rights to this invention pursuant to work funded thereby at Northwestern University.

BACKGROUND OF THE INVENTION

Delivering therapeutic drugs or cell therapies at a controlled release rate to a patient, or delivering encapsulated conductive or magnetic materials at a controlled rate and orientation to process are important goals in medicine and the emerging field of nanotechology manufacturing. Controlling the release of drugs can have a positive effect on therapeutic treatments by maintaining a constant level of the therapy in the patient and also eliminating the need for external intraveneous delivery means or risk of delaying or missing oral administrations of a therapy. Encapsulation can provide enhanced solubility or controlled reactivity for drugs, catalysts, or materials like carbon nanotubes. Micelles and self assembled micelles may allow for the controlled encapsulation and delivery of such materials.

The functional head groups from the molecules which form the micelle and encapsulate the material should interact favorably with the material to be encapsulated. The formed micelle, including the material, must also have the proper reactivity and solubility for its intended application. These properties are determined by the head groups on the molecules which are on the exterior of the micelle as well as the intermolecular bonding of the molecules comprising the micelle. For polar drugs, DNA, mineralizable inorganic salts, and other materials with high surface energies, an encapsulating matrix with a polar core is advantageous.

Bola amphiphiles are molecules in which two or more hydrophilic groups are connected by hydrophobic moieties. Many papers report using peptides as the polar headgroups for symmetrical bola amphiphiles—those in which the head groups are the same. Symmetrical bola-amphiphiles with GlyGly as the hydrophilic headgroups, using saturated hydrocarbon 1,7-heptane dicarboxylic acid have been made (Matsui, H.; Douberly, G. E. *Langmuir* 2001, 17, 7918-7922, and 1,12-dodecane dicarboxylic acid in Shimizu, T.; Kogiso, M.; Masuda, M. *J. Am. Chem. Soc.* 1997, 119, 6209-6210). A bola-amphiphile with ValVal as a hydrophilic head group for a bola amphiphile was reported by Kogiso, M.; Hanada, T.; Yase, K.; Shimizu, T. *Chem. Comm.* 1998, 17, 1791-1792. The dipeptides GlyGly, ProPro, SarSar and (N-methyl)Gly (N-methyl)Gly and the tripeptides GlyGlyGly, GlyProPro, and GlySarSar are the headgroups in a series of bola amphiphiles with 8-16 carbon hydrocarbon diacids as the hydrophobic spacer as reported in Kogiso, M.; Ohnishi, S.; Yase, K.; Masuda, M.; Shimizu, T. *Langmuir* 1998, 14, 4978-4986. The amino acids Ser, Glu, and Asp have also been reported in bola amphiphiles. Asymmetrical bola amphiphile are those amphiphiles where the hydrophilic groups differ in their hydrophilicity. Some examples of asymmetric bola amphiphiles include sugars, and the nucleosides A and T (Shimizu, T.; Iwaura, R.; Masuda, M.; Hanada, T.; Yase, K. *J. Am. Chem. Soc.* 2001, 123, 5947-5955). Other examples of asymmetrical bola amphiphiles include those prepared from Lys coupled to 12-amino dodecane carboxylic acid oligomers (Fuhrhop, J. H.; Spiroski, D.; Boettcher, C. *J. Am. Chem. Soc.* 1993, 115, 1600-1601) in which either rods or tubes are obtained. However, these rods do not bury a polar headgroup within the core of the cylindrical micelle.

There is a need in the art to be able to make self-assembling micelles from amphiphiles that have lyophilic groups at the core and outer surface of the micelle. It would be further desirable to control the structure, reactivity, and function of such micelles by modification of the amphiphile's molecular structure.

SUMMARY OF THE INVENTION

The present invention provides for bola amphiphiles compositions which have more than one lyophilic (hydrophilic) head group and a lyophobic (hydrophobic) moiety capable of hydrogen bonding with other bola amphiphiles. These bola amphiphiles are capable of self assembling into micelles. The advantage of these bola amphiphiles is that they may self-assemble into micelles whose lyophilic head groups are located within the core and on the surface of the micelles. The lyophilic environment at the core and on the surface of the micelles may be different and may be controlled by the choice of head group moieties on the bola amphiphiles. The utility of these compositions is that they can be used to load or encapsulate polar drugs, DNA, mineralizable inorganic salts, or other molecules of interest within the polar interior of the micelle. Such compositions may also provide small water-filled ion-conducting channels within their structure suitable for use in micro electromechanical devices, as templates for nanowires or dielectrics, and as chemical sensors.

BRIEF DESCRIPTION OF THE FIGURES

Various aspects and applications of the present invention will become apparent to the skilled artisan upon consideration of the brief description of the figures and the detailed description of the invention, which follows.

DESCRIPTION OF THE INVENTION

Figure 1:
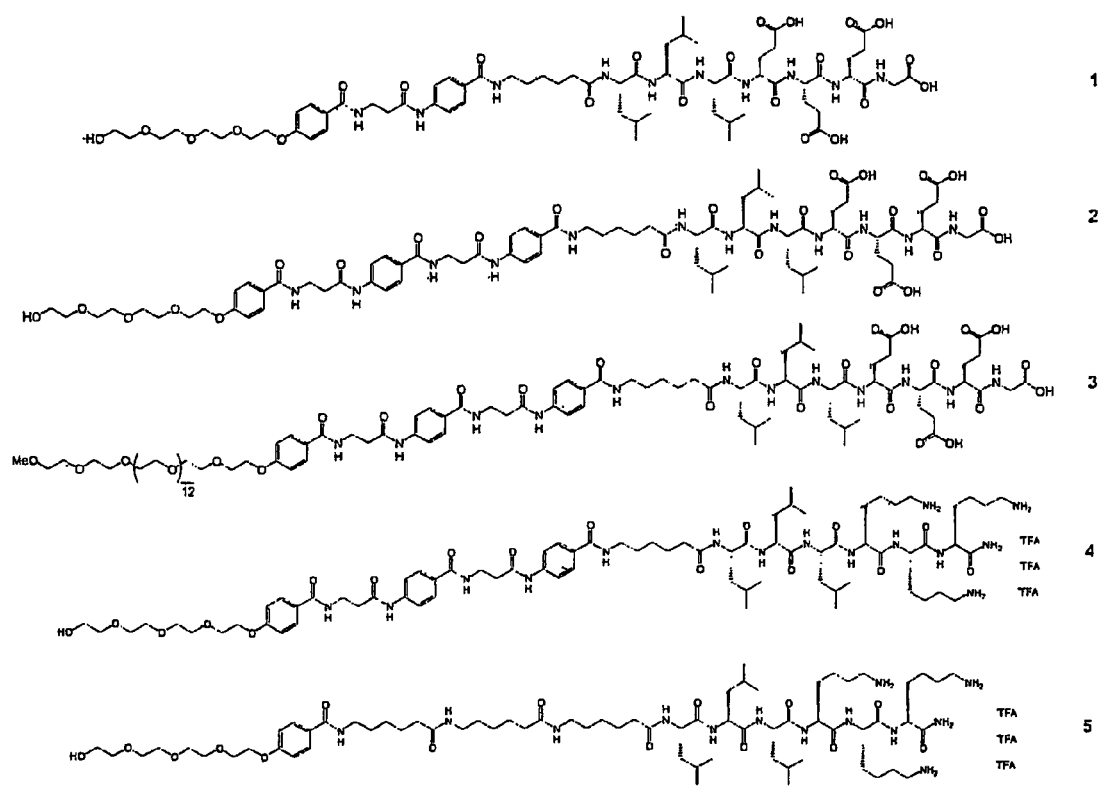
FIG. 1 is an illustration of the chemical structure of Bola peptide-amphiphiles, 1-5, containing single oligo(ethylene glycol) chains.

Cylindrical micelles or nanofibers comprised of self assembled peptide amphiphiles having a hydrophobic core and a hydrophilic shell have been made. The general concept of peptide-amphiphiles that self-assemble into cylindrical micelles have been reviewed in two articles: Hartgerink, J. D., Beniash, E., and Stupp, S. I. *Science* 2001, 294 (5547) 1684-1688 and Hartgerink, J. D., Beniash, E., and Stupp, S. I. *Proc. Nat. Acad. Sci.* 2002, 99 (8), 5133-5138, and are incorporated herein by reference in their entirety.

The addition of a second polar head group to an existing peptide amphiphile or peptide rod amphiphile would form a bola amphiphile and give a triblock structure to these molecules. These molecules would be characterized by two hydrophilic or lyophilic regions, which could be similar or dissimilar from one another, that sandwich a relatively hydrophobic or lyophobic section of the molecule. The lyophobic section of the bola amphiphile molecule is designed to have moieties or functional groups capable of intramolecular hydrogen bonding.

A bola amphiphile with a tri block structure may self assemble in aqueous solutions into a micelle where the lyophobic portion of the bola amphiphile is excluded from the aqueous solution and the lyophobic groups are directed to the core and surface of the micelle. In traditional aqueous self assembled peptide amphiphiles the lyophobic group is located at the core of the micelle.

The bola amphiphiles of the present invention create a new lyophilic, rather than lyophobic, core for self assembled micelles that are formed from them. One of the key advantages of such bola amphiphiles and micelle structures over existing bola-amphiphiles would be the presence of hydrogen bonding in the lyophobic region. This stabilizes the self-assembled structure, but also allows for changes in hydrogen-bonding patterns within the lyophobic region of the bola amphiphiles and micelles. This hydrogen bonding can be engineered to encourage a polar arrangement of adjacent molecules, and it may allow for control of the structure, reactivity, and hence function of the such micelles. A second advantage of these micelles may be that the lyophilic core provides functional groups for transporting ions along the core of the micelle. A water filled ion-conducting channel may function as a sensor. Self assembled bola amphipiles of this type may permit loading or encapsulation of polar drugs, bioactive peptides, DNA, mineralizable inorganic salts, or other molecules of interest within the polar interior of the micelles or nanofibers.

One object of the present invention is to provide for a bola amphiphile composition with a lyophobic moiety capable of hydrogen bonding and having a first end and a second end. The first end of the lyophobic moiety is chemically coupled to a first lyophilic head group moiety, and the second end of the lyophobic moiety is chemically coupled bonded to a second lyophilic head group. The molecule formed by the coupling of these groups is a bola amphiphile with a triblock structure. In such a bola amphiphile, the first and second lyophilic heads groups or moieties may have the same or different lyophophilicity. The lyophilic head groups may be peptides, and in a preferred embodiment the amino acids comprising the peptide have at least three non-peptide bond forming amine or acid moieties.

Figure 5:
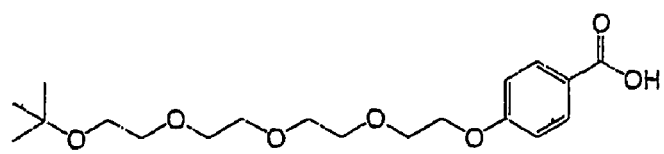
FIG. 5 is an illustration of the chemical building blocks, 14-20, for Bola peptide-amphiphiles.
Figure 5:
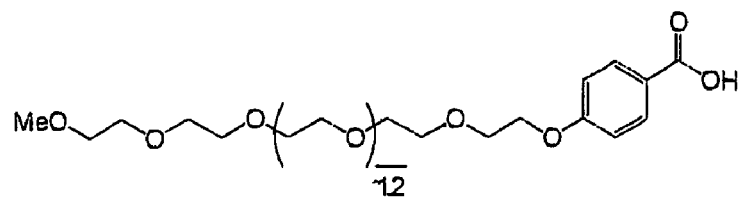
Figure 5:
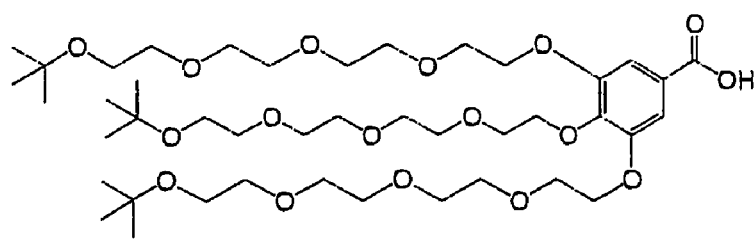
Figure 5:
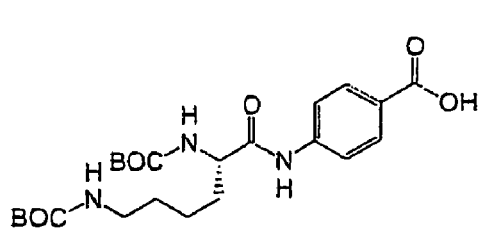
Figure 5:
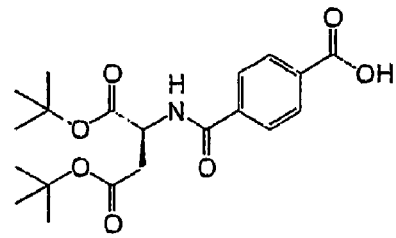
Figure 5:
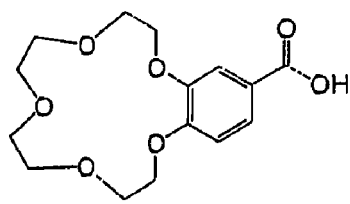
Figure 5:
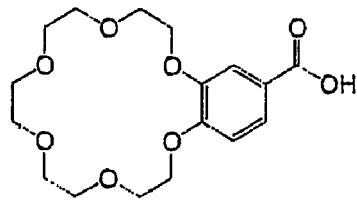

Other lyophilic head groups for the bola amphiphiles useful in the practice of this invention may be one or more oligo(ethylene glycol) chains, cyclic oligo(ethylene glycols), hydroxyl functionalities from amino acids such as those derived from L-serine, and potentially charged amino or carboxylic acid groups derived from Asp, Lys, 4'-amino-4-biphenyl carboxylic acid, p-amino benzoic acid, 6-aminohexanoic acid. The terminal building blocks 14-18, and crown ethers such as 19 and 20, shown in FIG. 5, are also useful in the practice of this invention.

The lyophobic group of the bola amphiphiles has functional groups capable of hydrogen bonding. Examples of groups which may be incorporated into the lyophibic portion of the bola amphiphile include but are not limited to p-amino benzoic acid, p-hydroxy benzoic acid, 4'-amino-biphenyl-4-carboxylic acid, cholesterol, and 6-amino-hexanoic acid. Lyophobic moieties in the bola amphiphile may also be comprised of alkenes, acetylenes, aromatics, and heteroaromatic moieties containing amine, acidic, and hydroxyl functionalities capable of hydrogen bonding. The degree of hydrogen bonding in the lyophobic portion of the bola amphiphile may be controlled by the number and types of groups chosen to make up the lyophobic group. For example, substitution of 7-amino-hexanoic acid for one or more of the 6-amino-hexanoic acid molecules in 5 would be expected to change the hydrogen bonding due to the greater aliphatic content of the 7-amino-hexanoic acid.

Another object of this invention is a composition that is a self assembled micelle comprising at least one bola amphiphile. Self assembled micelles can form in a variety of shapes including but not limited to spheres, cylinders, tubes, or disks. Micelles may be formed in water or aqueous solutions containing dissolved salts or other solvents like ethanol. In a preferred embodiment the bola amphiphiles forming the micelle have a lyophobic moiety capable of intermolecular hydrogen bonding with, for example, other lyophobic moieties from bola amphiphiles adjacent to it in a micelle. Lyophilic groups in the bola amphiphile are chemically coupled to opposite ends of the lyophobic moietie. Molecules 1-13 are examples of bola amphiphiles useful in the self assembly of micelles and in the practice of this invention. The lyophilic head groups of the bola amphiphiles which self assemble to form the micelle may be the same or different. In a self assembled solid packed micelle, one of the lyophilic head groups of the bola amphiphile is at the center of the micelle and the other lyophilic head group is oriented toward the outer surface of the micelle. The core and surface of the micelle are substantially lyophilic.

In a preferred embodiment of this invention, the self assembled micelles form with the lyophilic group of the bola amphiphile at the center of the micelle. In a more preferred embodiment, the self assembled micelles form the weakest lyophilic group of the bola amphiphile at the center of the micelle.

The bola amphiphile may be prepared as a solution my dissolving it in a suitable solvent. It may then be mixed with materials or therapies for encapsulation. Examples of therapies include pharmaceuticals, chemotherapeutics, immunosuppresents, anifungals, antibacterials, growth factors, vaccines, tissue/cell culture factors, and antibiotics. Examples of suitable materials include carbon nanotubes, colloidal metals, polymers, magnetic colloids, and semiconductors.

A method of making a self assembled micelle from bola amphiphile with a lyophobic moiety capable of hydrogen bonding includes the step of making a first solution of a suitable bola-amphiphile in a charged ionic form, mixing the first solution with a second composition which changes the pH of the first solution towards a neutral pH, and reacting the first solution and second composition until a gel forms. The second composition may be in the form of a solid, liquid, or gas. For example, basic solutions of carboxylate salt based bola amphiphiles gel in water when the pH is lowered, for example, by introduction of HCl vapor. Ammonium salt based bola amphiphiles gel in water when the pH is raised, for example, by exposure of the solution to ammonia vapor. Preferably the bola amphiphile has a lyophobic group capable of hydrogen bonding and the micelle formed has a lyophilic group at the center of the micelle.

It is another object of this invention to provide for a method of encapsulating a therapeutic treatment in formed by these bola amphiphiles. Preferably at least one therapeutic agent is mixed with a solution containing a bola amphiphile. This solution is gelled, or self assembled, into micelles of the bola amphiphile with the therapeutic treatment by raising or lower the pH of the solution. Preferably the bola amphiphile has a lyophobic group capable of hydrogen bonding and the micelle formed has a lyophilic group at the center of the micelle.

It is another object of this invention to provide for a method of treating a patient with a therapeutic agent encapsulated in a self assembled bola amphiphile. The method includes the steps of identifying a site in need of treatment on a patient, and then administering an effective amount of the therapeutic agent encapsulated in the self assembled bola amphiphile micelles to the site. The micelle encapsulated therapy may be mixed with suitable carriers, made into pills, or mixed with other solutions for administering to the patient.

It is another object of this invention to provide for a method of encapsulating a carbon nanotube in a bola amphiphile. The method includes mixing carbon nanotubes with a solution of a bola amphiphile capable of self assembly. This mixture is gelled, or self assembled, into micelles of the bola amphiphile with the carbon nanotubes by raising or lower the pH of the solution. Preferably the bola amphiphile has a lyophobic group capable of hydrogen bonding and the micelle formed has a lyophilic group at the center of the micelle.

Figure 2:
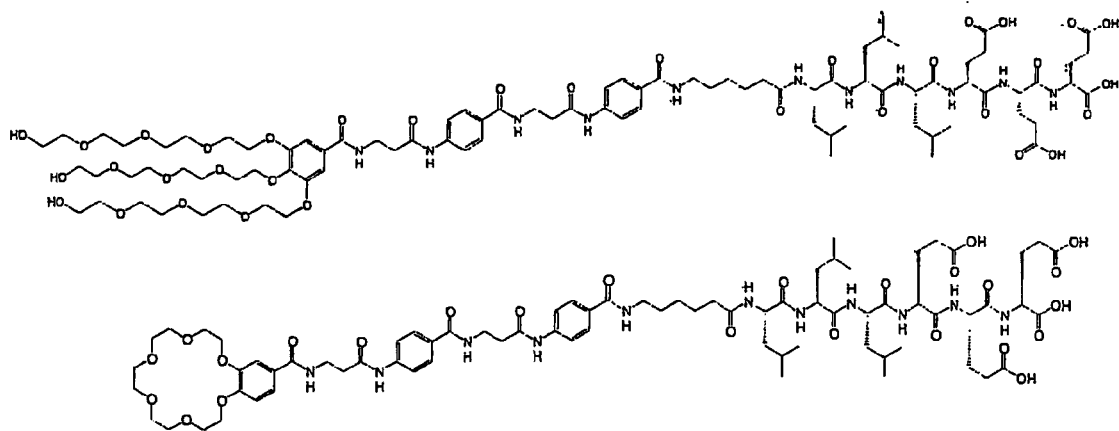
FIG. 2 is an illustration of the chemical structure of Bola peptide-amphiphiles, 6 and 7, containing multiple or cyclic oligo(ethylene glycol) chains.
Figure 3:
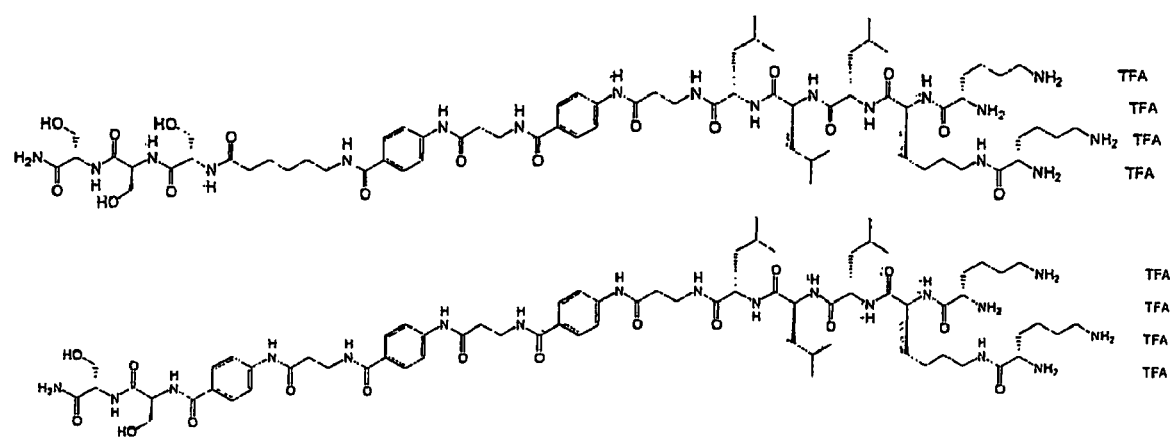
FIG. 3 is an illustration of the chemical structure of Bola peptide-amphiphiles, 8 and 9, containing hydroxyls from L-Serine.
Figure 4:
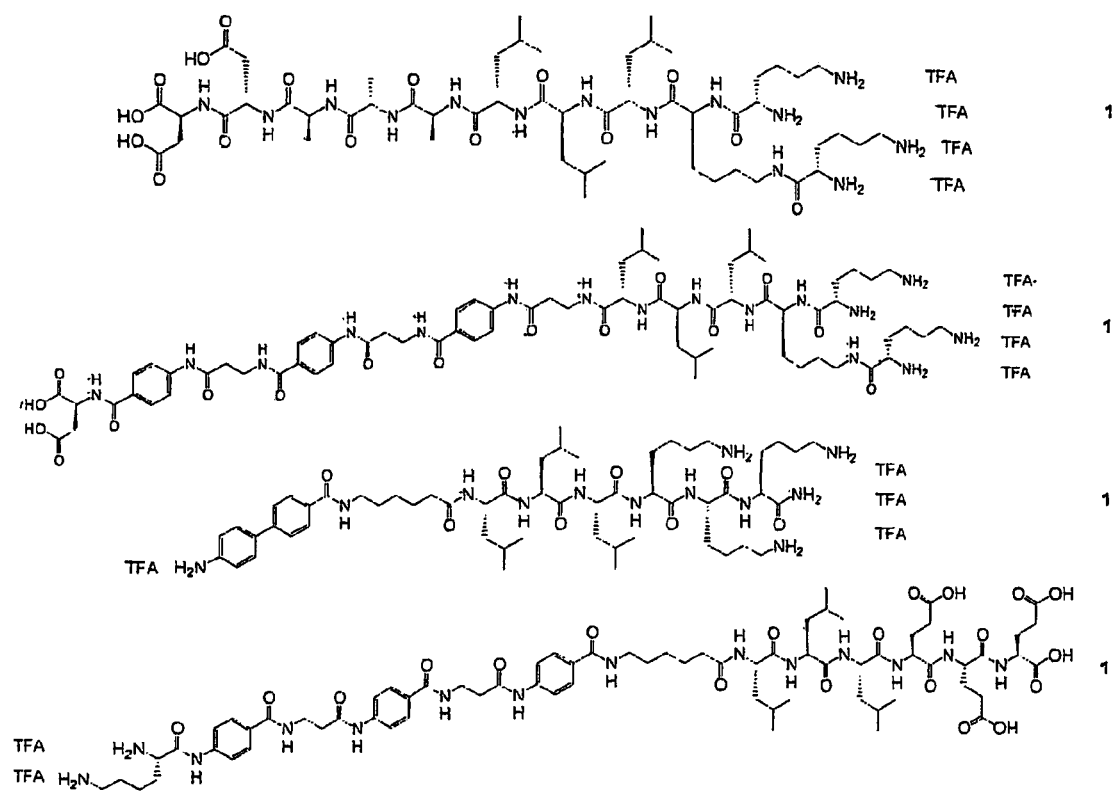
FIG. 4 is an illustration of the chemical structure of Bola peptide-amphiphiles, 10-13, with charged headgroups from amino or acid group at both termini.
Figure 6:
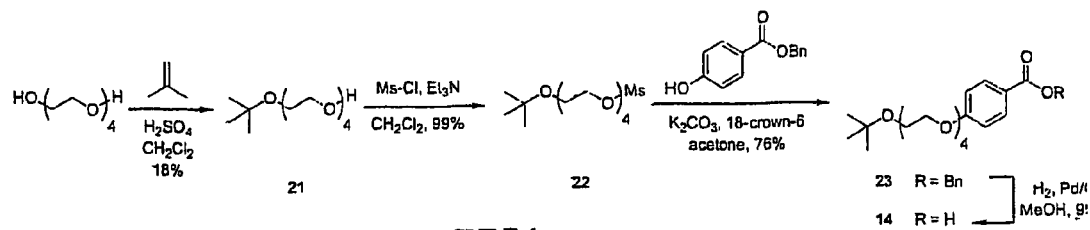
FIG. 6 is an illustration of synthesis of terminal tetraethylene glycol acid 14.
Figure 7:
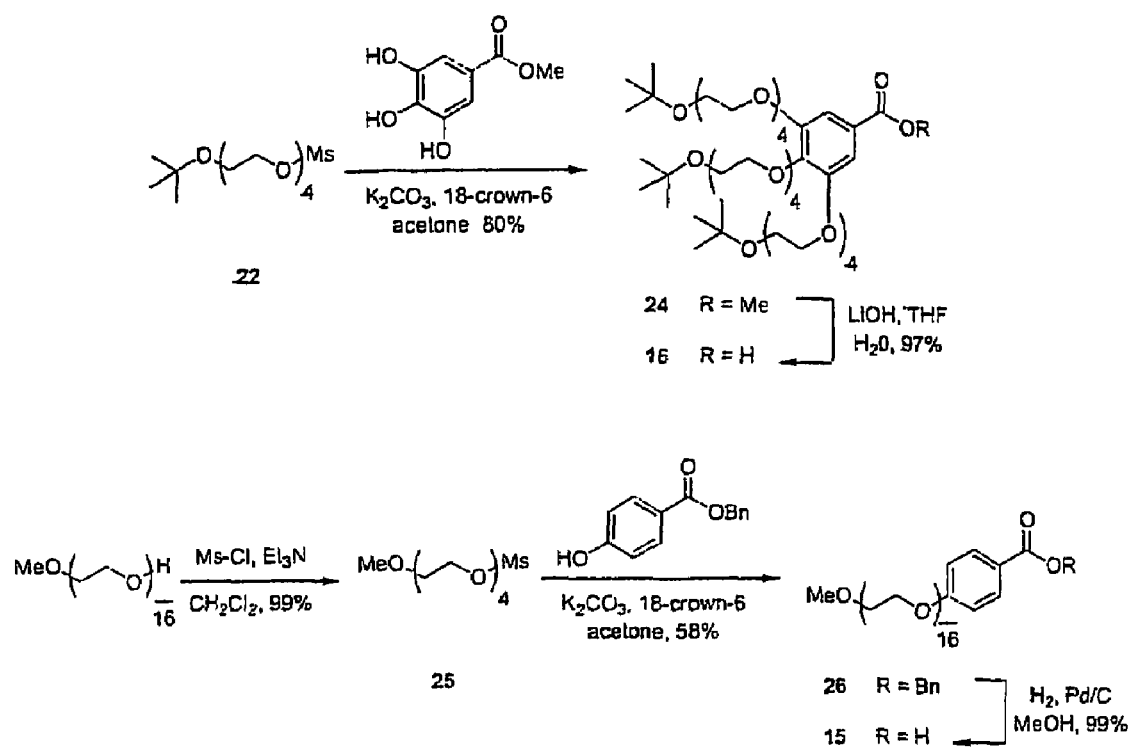
FIG. 7 is an illustration of the synthesis of the terminal building blocks 15 and 16.
Figure 8:
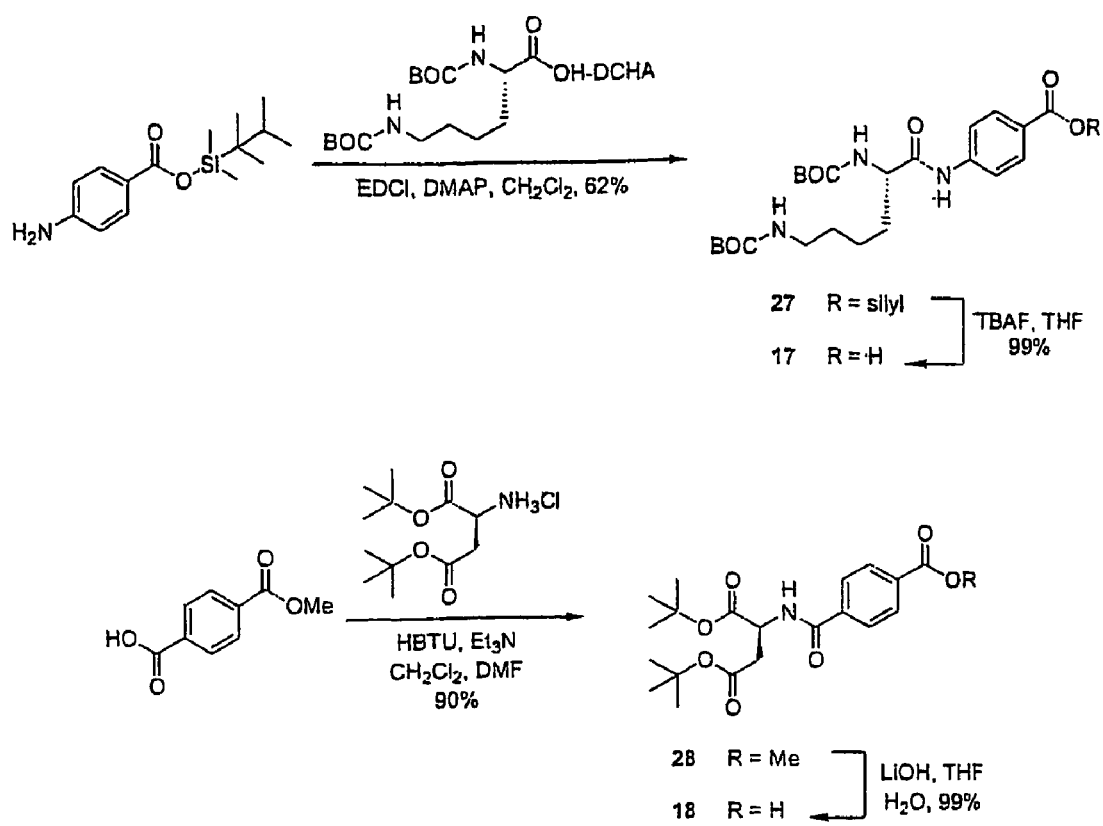
FIG. 8 is an illustration of the synthesis of the terminal building blocks 17 and 18.

The bola PA's are prepared by solid-phase peptide synthetic techniques, using the Fmoc strategy from Rink, preloaded Wang, or preloaded HMPB resins. The bola amphiphiles presented in this disclosure are all of the unsymmetrical variety, although symmetrical ones can be prepared in a similar manner. The exterior headgroups are designed to have three to four amino or carboxylic acid charges, and the interior headgroups are designed to have one oligo(ethylene glycol) chain (1-5 in FIG. 1), multiple or cyclic oligo(ethylene glycol) chains (6 and 7 in FIG. 2), hydroxyl functionalities derived from L-serine (8 and 9 in FIG. 3), and the potentially charged amino or carboxylic acid groups derived from Asp, Lys (K), or 4'-amino-4-biphenyl carboxylic acid (10-13 in FIG. 4). The amino acid residues used in these bola PA's are naturally occurring and commercially available with the exception of p-aminobenzoic acid (PABA), used as an Fmoc-beta-Ala-PABA-COOH dimer reported in a previous disclosure, 6-aminohexanoic acid, and the terminal building blocks 14-20 outlined in FIG. 5. The solution phase syntheses of the terminal building blocks 14-18 are described in FIGS. 6-8, and crown ethers 19 and 20 are commercially available.

The bola PA's can be gelled in the same manner previously described for the original PA's and the peptide rod amphiphiles. The bola PA's with exterior polar amino acid headgroups of KKK or second generation Lys dendrons are cleaved from the resin as their TFA salts and are freely soluble in water, with the exception of insoluble 10, and are gelled by exposing a 0.2-1.5% by wt solution in water to ammonia vapors. The bola PA's with exterior headgroups of EEE (E=Glu) and EEEG (G=Gly) are charged as their potassium carboxylates by dissolving them in 0.1 N KOH solution at concentrations of 0.2-1.5% by wt, and are gelled by exposure to HCl vapors. Table 1 qualitatively outlines the results of the gelation experiments under these conditions.

TABLE 1

Gelation of the Bola PA's by change in pH.

| Bola PA | wt % | gelation behavior | clarity |
|---|---|---|---|
| 1 | 1.0 | self-supporting gel | clear |
|  | 0.77 | self-supporting gel | clear |
| 2 | 1.0 | self-supporting gel | opaque/cloudy |
|  | 0.5 | self-supporting gel | opaque/cloudy |
| 3 | 1.0 | weak gel | opaque |
|  | 0.5 | weak gel | cloudy |
| 4 | 1.0 | self-supporting gel | clear |
|  | 0.5 | self-supporting gel | clear |
|  | 0.25 | self-supporting gel | clear |
| 5 | 1.0 | weak gel | cloudy |
|  | 0.5 | weak gel pellet | cloudy |
|  | 0.25 | precipitates | cloudy |
| 6 | 1.5 | self-supporting gel | opaque/cloudy |
|  | 1.0 | self-supporting gel | opaque/cloudy |
|  | 0.5 | fragile gel | cloudy |
|  | 0.25 | precipitates | cloudy |
| 7 | 1.0 | self-supporting gel | cloudy |
|  | 0.5 | self-supporting gel | cloudy |
|  | 0.25 | fragile gel | cloudy |
| 8 | 1.0 | fragile gel | cloudy |
|  | 0.5 | viscous solution | clear |
| 9 | 1.0 | self-supporting gel | clear |
|  | 0.5 | self-supporting gel | clear |
|  | 0.25 | self-supporting gel | clear |
| 11 | 1.0 | precipitates | cloudy |
|  | 0.5 | precipitates | cloudy |
| 12 | 1.0 | self-supporting gel | slightly cloudy |
|  | 0.3 | self-supporting gel | clear |
| 13 | 1.0 | self-supporting gel | slightly cloudy |
|  | 0.5 | self-supporting gel | clear |
|  | 0.25 | self-supporting gel | clear |

Figure 9:
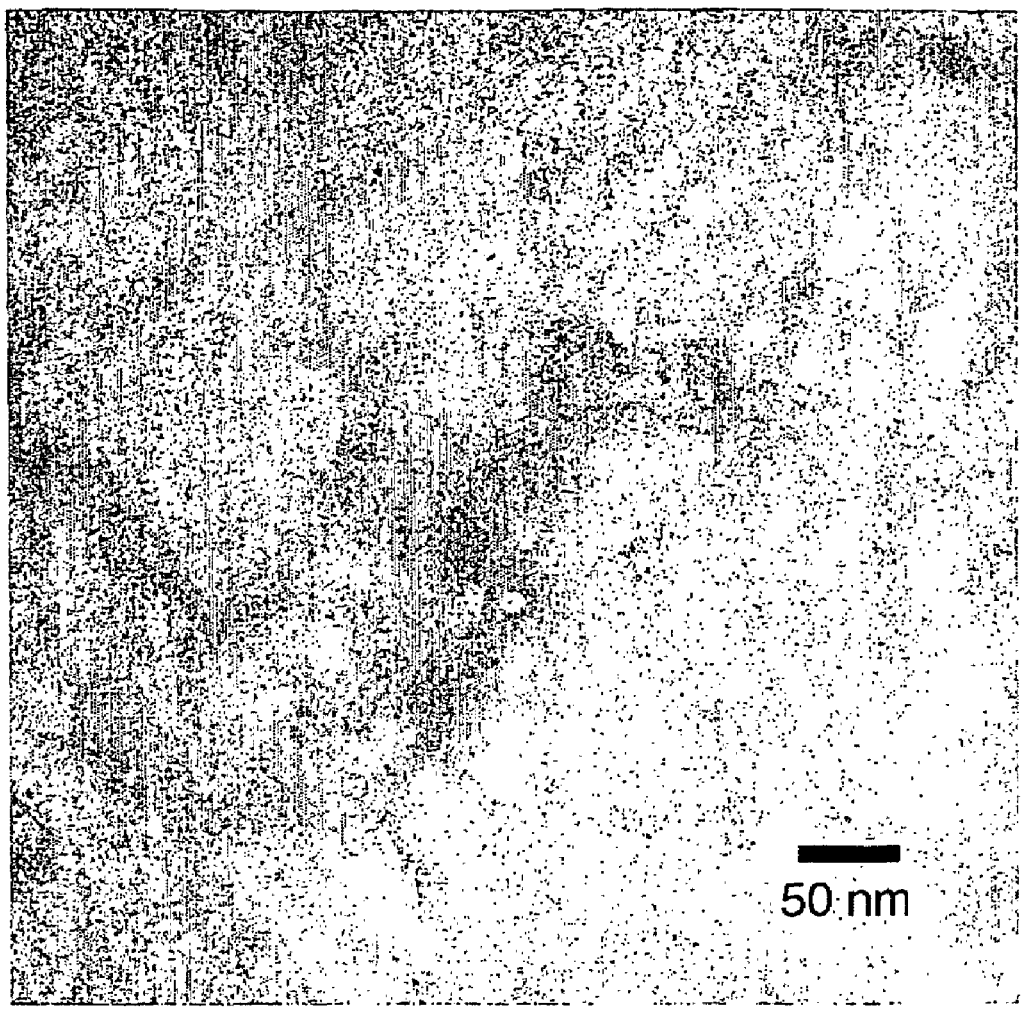
FIG. 9 is a TEM image of 2 without staining.
Figure 10:
FIG. 10 is a TEM image of 2 negatively stained with phosphotungstic acid.
Figure 11:
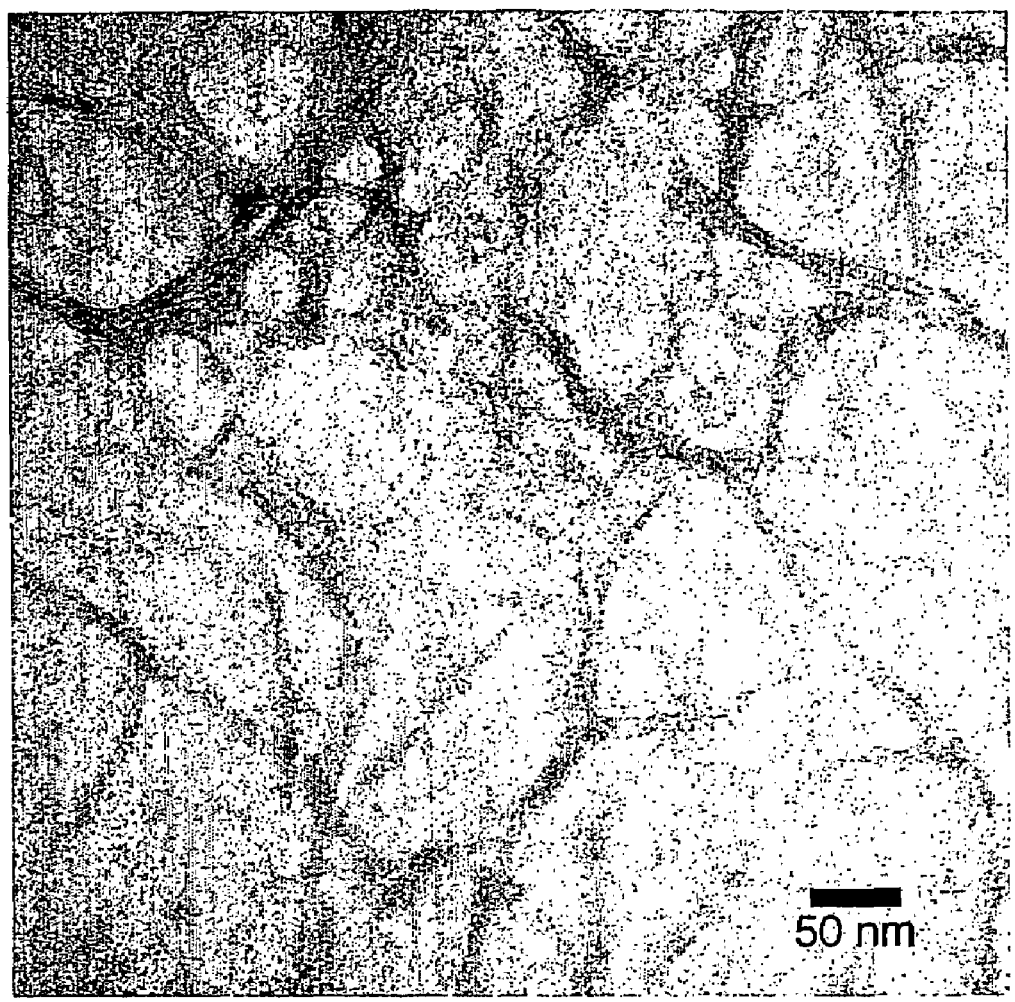
FIG. 11 is a TEM image of 2 positively stained with uranyl acetate.
Figure 12:
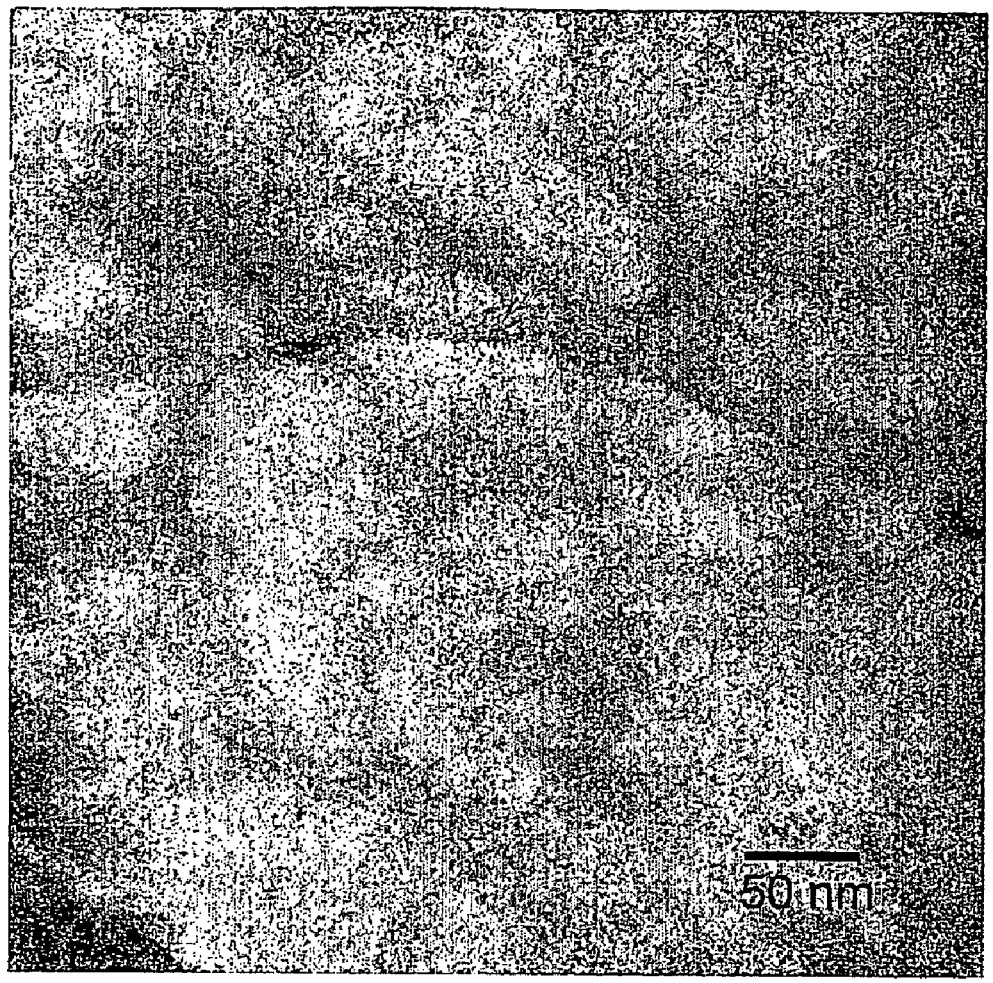
FIG. 12 is a TEM image of 4 negatively stained with phosphotungstic acid.
Figure 13:
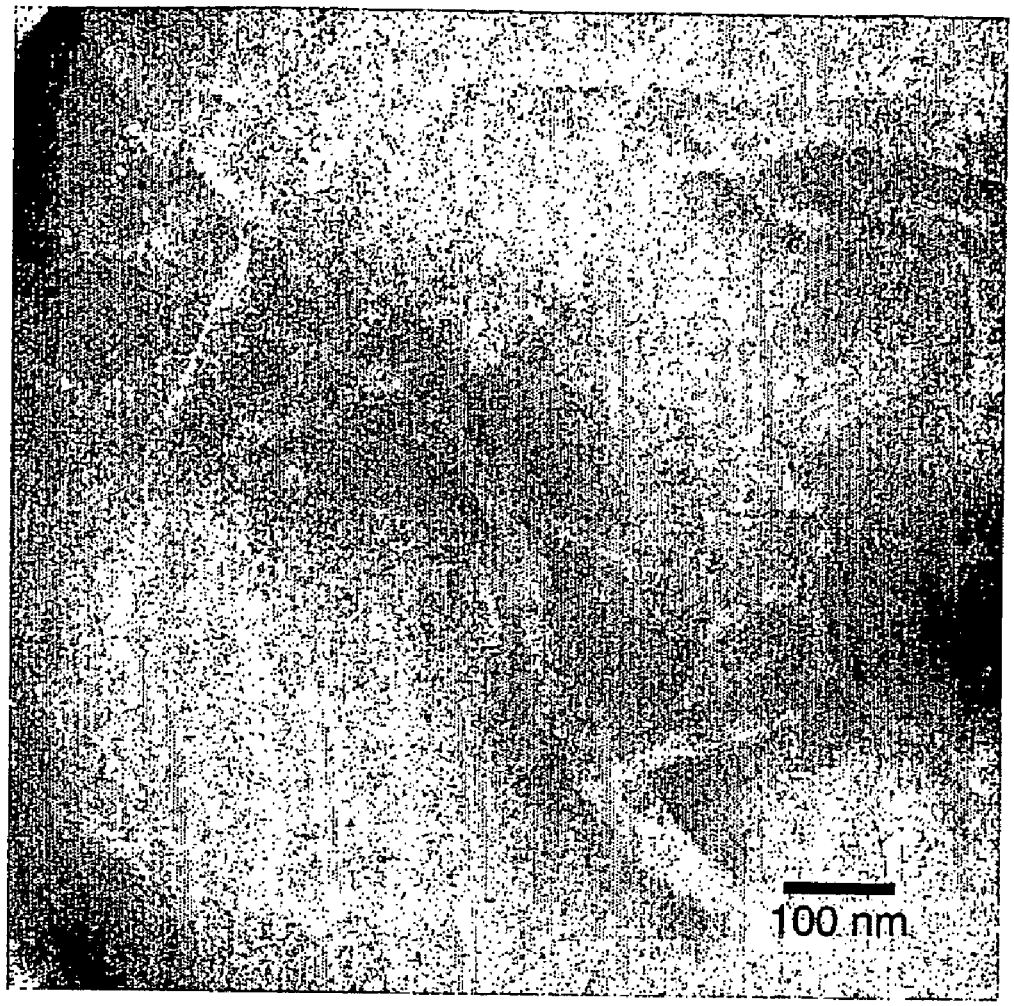
FIG. 13 is a TEM image of 6 negatively stained with phosphotungstic acid.
Figure 14:
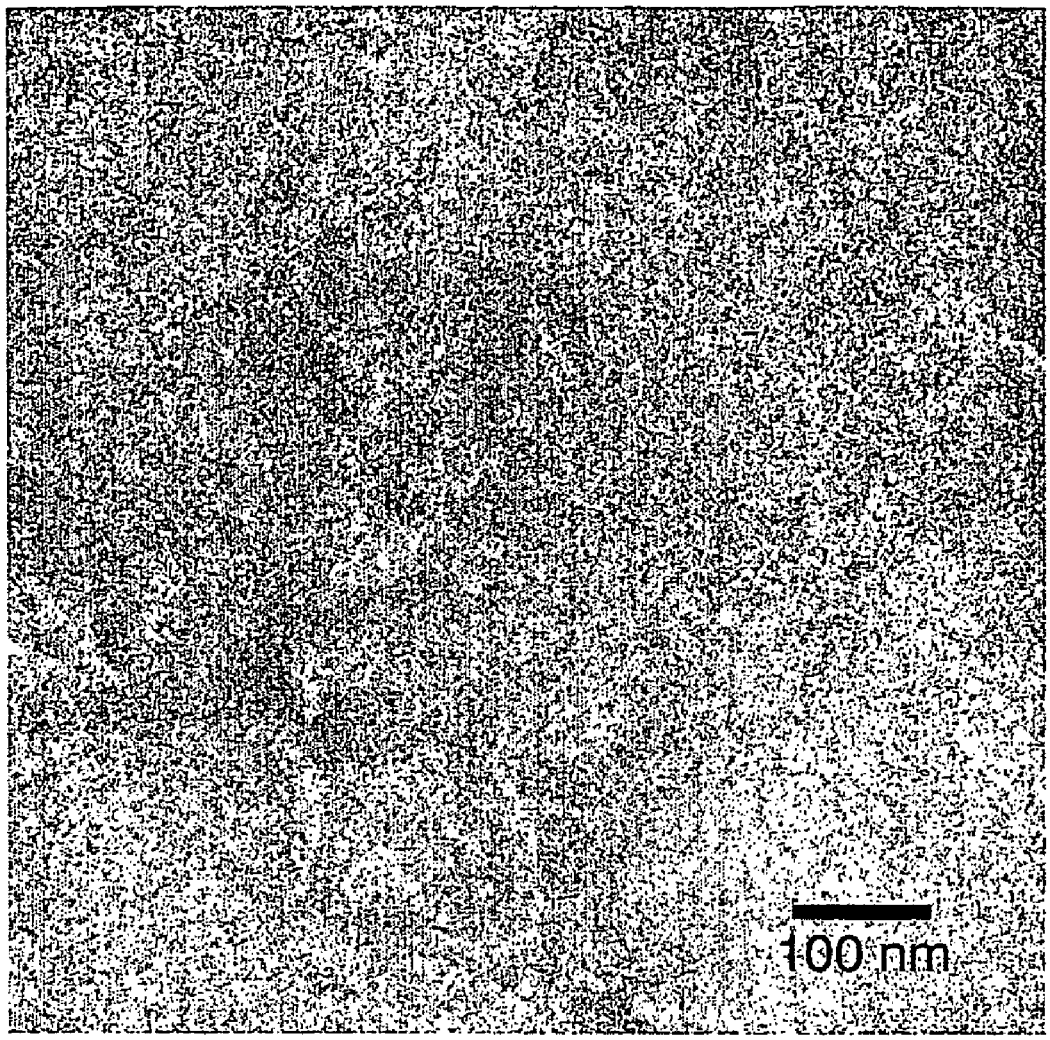
FIG. 14 is a TEM image of 7 negatively stained with phosphotungstic acid.

The structures of the 1.0% by wt gels of bola PA's 2, 4, 6, and 7 were investigated by TEM. The single tetraethylene glycol chains at the core with EEEG and KKK amino acid sequences at the periphery, in 2 and 4, respectively, show predominantly nanofiber-like structures of roughly twice the calculated length of the bola PA. Bola PA 2 is shown in FIGS. 9, 10, and 11 without staining, with negative staining, and with positive staining, respectively. (At this time the data does not absolutely exclude a flat ribbon structure.) The TEM image of 4 negatively stained with phosphotungstic acid is shown in FIG. 12. Positive staining with uranyl acetate, as in FIG. 11, demonstrates the polar arrangement of ethylene glycol chains at the core and carboxylic acid functionalities at the periphery of the fibers, with the carboxylic acids preferentially stained. Unlike 2 and 4 with a single tetraethylene glycol chain, the negatively stained TEM images of 6 with three chains and 7 with a crown ether in FIGS. 13 and 14, respectively, show less defined fiber structure. Spherical micelles are observed in FIG. 14, in addition to the one-dimensional fiber-like structures. The use of the more crowded ethylene glcyol polar headgroups in 6 and 7 appears to disrupt the cylindrical micelle structure, so that the peptide region would need to be redesigned with a larger cross-sectional area if these headgroups are to be accommodated at the core.

Uses for the self assembled bola amphiphiles include but are not limited to encapsulation and delivery of therapeutics, tissue engineering, formation of ion channels for sensors and cell therapies, formation of nanowires, and pH responsive cylindrical micelles for the release of micelle-encapsulated materials and the capture of material dissolved in the solution.

The advantage of these materials is that they self-assemble into cylindrical micelles whose hydrophilic environments, both within the core of the cylinder and at its periphery, are different and can be controlled by the choice of amino acids or functionalized acid moieties on the bola amphiphiles.

Although the present invention has been described in considerable detail with reference to certain preferred versions thereof, other versions are possible. For example, . . . , Therefore, the spirit and scope of the appended claims should not be limited to the description of the preferred versions contained herein.

What is claimed is:

1. A triblock bola amphiphile composition comprising: a triblock bola amphiphile and a solvent, wherein the triblock bola amphiphile comprises a lyophobic moiety capable of hydrogen bonding and having a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains or cyclic oligo(ethylene glycols) chains and the other lyophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine.

2. The bola amphiphile as in claim 1, wherein one lyophilic head group is oligo(ethylene glycol) chains and the other lyophilic head group comprises an amino acid sequence of glutamic acid-glutamic acid-glutamic acid.

3. A self assembled micelle comprising: at least one triblock bola amphiphile, said triblock bola amphiphile having a lyophobic moiety capable of hydrogen bonding and having a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains and cyclic oligo(ethylene glycols) chains, and the other lyophilic head group comprises an amino acid sequence comprising hydroxyl functionalities from L-serine, charged amino or carboxylic acid groups derived from aspartic acid or lysine, or the amino acid sequence, glutamic acid-glutamic acid-glutamic acid or lysine-lysine-lysine.

4. The micelle of claim 3 wherein the lyophilic head groups of the bola amphiphile are different.

5. The micelle of claim 3 wherein the core of the micelle is lyophilic.

6. The micelle of claim 3 wherein the one or more bola amphiphiles comprising the micelle are capable of hydrogen bonding.

7. A method of making a self assembled micelle from triblock bola amphiphile with a lyophobic moiety capable of hydrogen bonding and having a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains and cyclic oligo(ethylene glycols) chains, and the other lyophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine, comprising the steps of: making a first solution of the triblock bola-amphiphile in a charged ionic form; mixing the first solution with a second composition which changes the pH of the first solution towards a neutral pH; and reacting the first and second solutions until a gel forms.

8. A method of encapsulating a therapeutic agent comprising: providing a therapeutic agent; exposing said therapeutic agent to a bola amphiphile capable of self assembly, wherein the bola amphiphile comprises a lyophobic moiety capable of hydrogen bonding, the amphiphile having a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains and cyclic oligo(ethylene glycols) chains, and the other lyophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine; and initiating self assembly.

9. A method of treating a patient in need thereof with a therapeutic agent encapsulated in a self assembled bola amphiphile, wherein the bola amphiphile comprises a lyophobic moiety capable of hydrogen bonding, the amphiphile having a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains and cyclic oligo(ethylene glycols) chains, and the other lyophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine, comprising: identifying a site on a patient in need of a treatment; and administering the bola amphiphile encapsulated therapeutic agent to said site.

10. A method of encapsulating a nanotube comprising: forming a nanotube; exposing said nanotube to a bola amphiphile capable of self assembly and comprising a lyophobic moiety capable of hydrogen bonding, the bola amphiphile having a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains and cyclic oligo(ethylene glycols) chains, and the other lyophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine, and initiating self assembly of said bola amphiphile.

11. A triblock bola amphiphile composition comprising: a solvent and a hydrophobic moiety capable of hydrogen bonding and having a first end and a second end; the first end of said hydrophobic moiety chemically coupled to a first hydrophilic head group; and the second end of said hydrophobic moiety chemically coupled to a second hydrophilic head group, wherein one hydrophilic head group is selected from the group consisting of oligo(ethylene glycol) chains and cyclic oligo(ethylene glycols) chains and the other hydrophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine.

12. A self assembled micelle comprising: at least one bola amphiphile, said bola amphiphile having a hydrophobic moiety capable of hydrogen bonding and having a first end and a second end; the first end of said hydrophobic moiety chemically coupled to a first hydrophilic head group; and the second end of said hydrophobic moiety chemically coupled to a second hydrophilic head group, wherein one hydrophilic head group is selected from the group consisting of oligo (ethylene glycol) chains and cyclic oligo(ethylene glycols) chains—and the other hydrophilic head group comprises an amino acid sequence comprising hydroxyl functionalities from L-serine, charged amino or carboxylic acid groups derived from aspartic acid or lysine, or an amino acid sequence selected from glutamic acid-glutamic acid-glutamic acid and lysine-lysine-lysine.

13. The micelle of claim 12 wherein the hydrophilic head groups of the bola amphiphile are different.

14. The micelle of claim 12 wherein the core of the micelle is hydrophilic.

15. The micelle of claim 12 wherein the at least one bola amphiphiles comprising the micelle are capable of hydrogen bonding.

16. A method of making a self assembled micelle from bola amphiphile with a hydrophobic moiety capable of hydrogen bonding, wherein the bola amphiphile has a first end and a second end; the first end of said lyophobic moiety chemically coupled to a first lyophilic head group; and the second end of said lyophobic moiety chemically coupled to a second lyophilic head group, wherein one lyophilic head group is selected from the group consisting of oligo(ethylene glycol) chains and cyclic oligo(ethylene glycols) chains, and the other lyophilic head group comprises an amino acid sequence comprising hydroxyl functionalities from L-serine, charged amino or carboxylic acid groups derived from aspartic acid or lysine, or the amino acid sequence selected from glutamic acid-glutamic acid-glutamic acid and lysine-lysine-lysine, comprising the steps of: making a first solution of the triblock bola-amphiphile in a charged ionic form; mixing the first solution with a second composition which changes the pH of the first solution towards a neutral pH; and reacting the first and second solutions until a gel forms.

17. The micelle as in claim 3, further comprising a composition chosen from the group consisting of: pharmaceuticals, chemotherapeutics, immunosuppresents, antifungals, antibacterials, growth factors, vaccines, tissue/cell culture factors, and antibiotics.

18. The micelle as in claim 3, further comprising a material chosen from the group consisting of: carbon nanotubes, colloidal metals, conductive polymers, magnetic colloids, and semiconductors.

19. The micelle as in claim 12, further comprising a composition chosen from the group consisting of: pharmaceuticals, chemotherapeutics, immunosuppresents, antifungals, antibacterials, growth factors, vaccines, tissue/cell culture factors, and antibiotics.

20. The micelle as in claim 12, further comprising a material chosen from the group consisting of: carbon nanotubes, colloidal metals, conductive polymers, magnetic colloids, and semiconductors.

* * * * *

UNITED STATES PATENT AND TRADEMARK OFFICE
CERTIFICATE OF CORRECTION

| | | |
|---|---|---|
| PATENT NO. | : 7,683,025 B2 | Page 1 of 1 |
| APPLICATION NO. | : 10/534266 | |
| DATED | : March 23, 2010 | |
| INVENTOR(S) | : Samuel I. Stupp et al. | |

It is certified that error appears in the above-identified patent and that said Letters Patent is hereby corrected as shown below:

In column 1, line 7, after "This application" please insert --is a 371 national phase application of PCT/US2003/036397, filed November 14, 2003, which--;

In column 1, line 11, please change "60/425,689 filed Nov. 12, 2002" to --60/426,189, filed Nov. 14, 2002--;

In column 1, please delete lines 12-17, as the government has no rights to this invention.

Signed and Sealed this

Thirty-first Day of August, 2010

David J. Kappos
*Director of the United States Patent and Trademark Office*